US009919139B2

(12) United States Patent
Tanaka et al.

(10) Patent No.: US 9,919,139 B2
(45) Date of Patent: Mar. 20, 2018

(54) SHEET SHAPED THERAPEUTIC SUBSTANCE TRANSFER APPARATUS AND METHOD OF AFFIXING SHEET SHAPED THERAPEUTIC SUBSTANCE

(71) Applicant: Tokyo Women's Medical University, Tokyo (JP)

(72) Inventors: Nobuyuki Tanaka, Tokyo (JP); Nobuo Kanai, Tokyo (JP); Masayuki Yamato, Tokyo (JP); Teruo Okano, Tokyo (JP)

(73) Assignee: Tokyo Women's Medical University, Tokyo (JP)

( * ) Notice: Subject to any disclaimer, the term of this patent is extended or adjusted under 35 U.S.C. 154(b) by 210 days.

(21) Appl. No.: 14/438,256

(22) PCT Filed: Oct. 23, 2013

(86) PCT No.: PCT/JP2013/078645
§ 371 (c)(1),
(2) Date: Apr. 24, 2015

(87) PCT Pub. No.: WO2014/069292
PCT Pub. Date: May 8, 2014

(65) Prior Publication Data
US 2015/0283364 A1    Oct. 8, 2015

(30) Foreign Application Priority Data
Oct. 31, 2012 (JP) .................................. 2012-240774

(51) Int. Cl.
*A61M 35/00* (2006.01)
*A61F 2/00* (2006.01)
(Continued)

(52) U.S. Cl.
CPC ............... *A61M 35/00* (2013.01); *A61B 1/06* (2013.01); *A61F 2/0063* (2013.01); *A61F 2002/0072* (2013.01); *A61F 2002/044* (2013.01)

(58) Field of Classification Search
CPC ...... A61M 35/00; A61M 25/10; A61F 2/0063; A61F 2002/0072; A61F 2002/044; A61B 1/06
See application file for complete search history.

(56) References Cited

U.S. PATENT DOCUMENTS 5,309,896 A * 5/1994 Moll ................. A61B 17/00234
128/898
5,766,151 A * 6/1998 Valley .............. A61B 17/00234
604/103.07
(Continued)

FOREIGN PATENT DOCUMENTS

JP    H02-239874 A    9/1990
JP    2008-079783 A    4/2008
(Continued)

OTHER PUBLICATIONS

Extended European Search Report, issued by the European Patent Office (EPO) dated Jul. 11, 2016, in connection with rresponding European Patent Application No. 13850668.8.
(Continued)

*Primary Examiner* — Timothy J Neal
(74) *Attorney, Agent, or Firm* — Edwards Neils LLC; Paul F. Neils

(57) ABSTRACT

With the present invention the sheet shaped therapeutic substance can be accurately and easily affixed to the inside of the human body. As shown in FIG. 6A, the sheet shaped substance can be mounted on the head with wrinkles being formed. When this takes place, the sheet shaped substance is held in contact with the outer periphery of the head. Then,
(Continued)

by making the pressure of the fluid inside the vent apertures positive, the sheet shaped substance can be blown off. The surface of the head is closely parallel to an inner surface of the esophagus wall for the sheet shaped substance to be affixed. Therefore, this particularly makes it possible to perform such applying step (FIG. 6B) in a more reliable fashion.

3 Claims, 26 Drawing Sheets

(51) Int. Cl.
*A61B 1/06* (2006.01)
*A61F 2/04* (2013.01)

(56) References Cited

U.S. PATENT DOCUMENTS

| | | | | |
|---|---|---|---|---|
| 5,836,311 | A * | 11/1998 | Borst | A61B 17/02 128/897 |
| 7,645,269 | B2 * | 1/2010 | Zamierowski | A61M 1/0088 604/305 |
| 8,920,403 | B2 * | 12/2014 | Doerr | A61M 25/0017 604/102.01 |
| 9,549,848 | B2 * | 1/2017 | Schneider | A61F 9/007 |
| 2001/0001812 | A1 * | 5/2001 | Valley | A61B 17/12022 604/96.01 |
| 2001/0044591 | A1 * | 11/2001 | Stevens | A61M 1/3659 604/6.11 |
| 2003/0229263 | A1 * | 12/2003 | Connors | A61B 5/205 600/29 |
| 2004/0236366 | A1 * | 11/2004 | Kennedy, II | A61M 25/10 606/192 |
| 2006/0259074 | A1 * | 11/2006 | Kelleher | A61B 17/04 606/213 |
| 2008/0269771 | A1 * | 10/2008 | Fulcher | A61F 2/142 606/107 |
| 2010/0145224 | A1 * | 6/2010 | Lee | A61M 25/10 600/562 |
| 2010/0222802 | A1 * | 9/2010 | Gillespie, Jr. | A61B 90/02 606/192 |
| 2011/0092998 | A1 * | 4/2011 | Hirszowicz | A61F 5/003 606/192 |
| 2014/0276044 | A1 * | 9/2014 | Sproul | A61M 5/007 600/435 |
| 2015/0305943 | A1 * | 10/2015 | Hossainy | A61F 11/002 604/514 |

FOREIGN PATENT DOCUMENTS

| | | |
|---|---|---|
| JP | 2008-148887 A | 7/2008 |
| JP | 2008-173333 A | 7/2008 |
| JP | 2010-082026 A | 4/2010 |
| WO | 2012018006 A1 | 2/2012 |

OTHER PUBLICATIONS

International Search Report issued in PCT/JP2013/078645 dated Dec. 24, 2013.

* cited by examiner

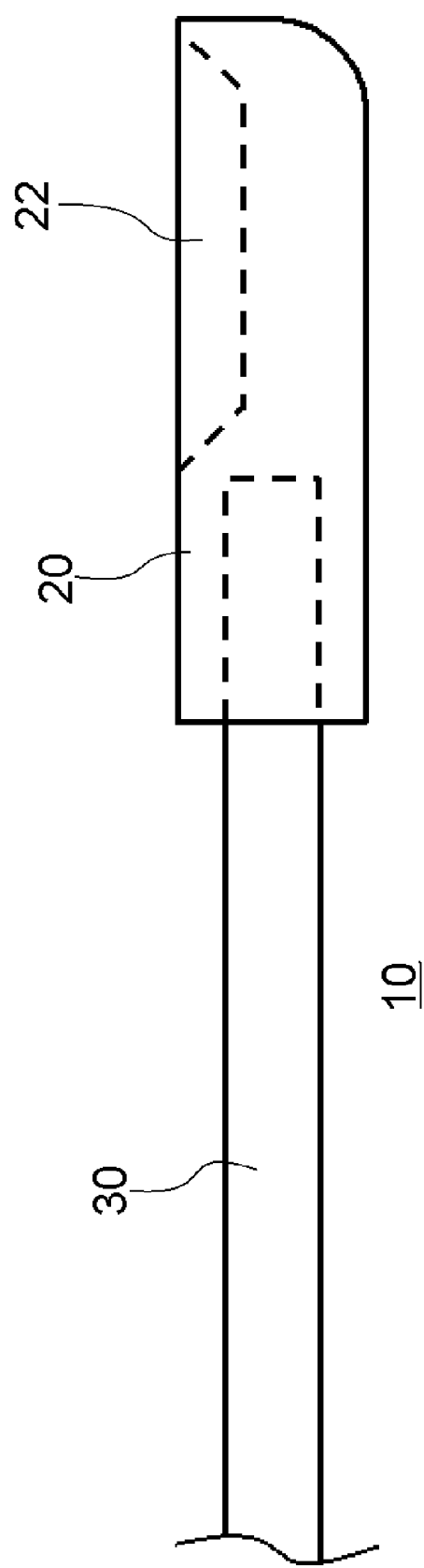

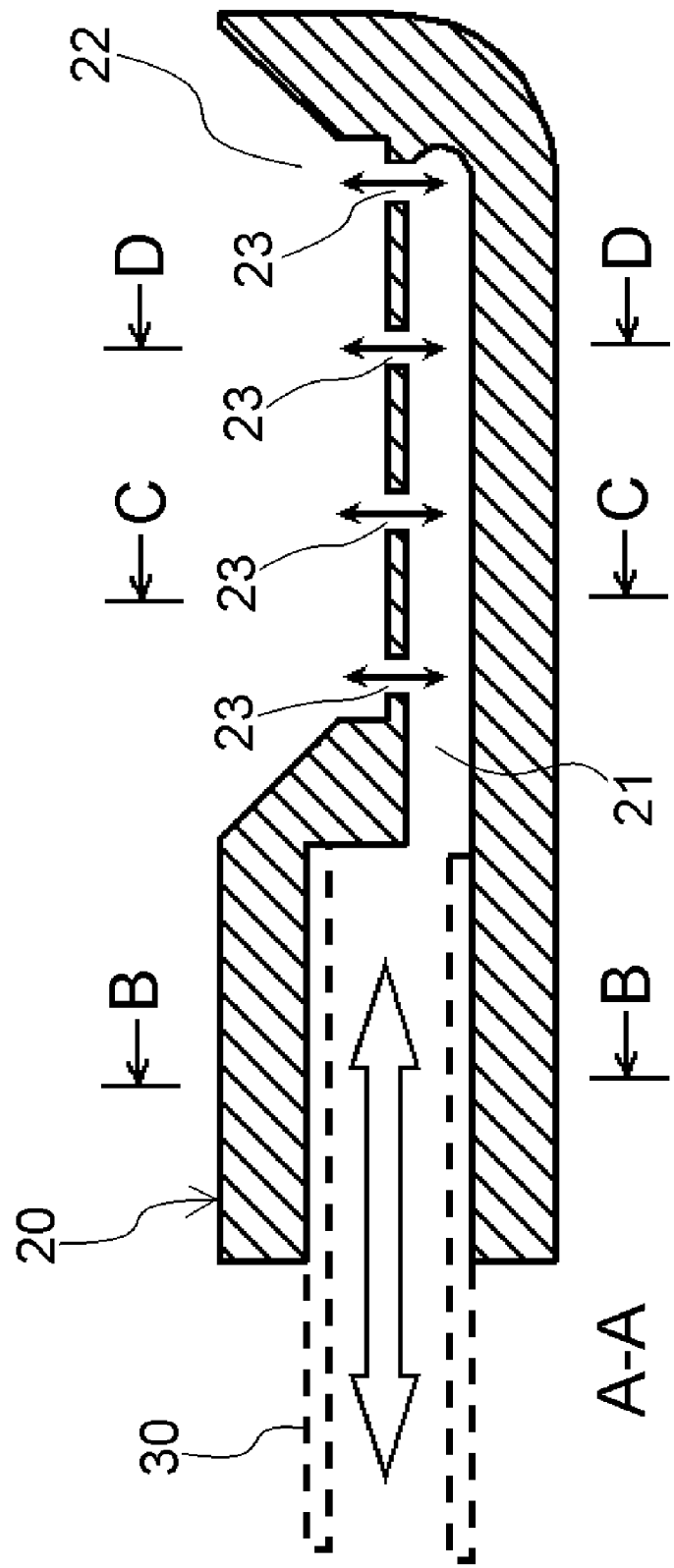

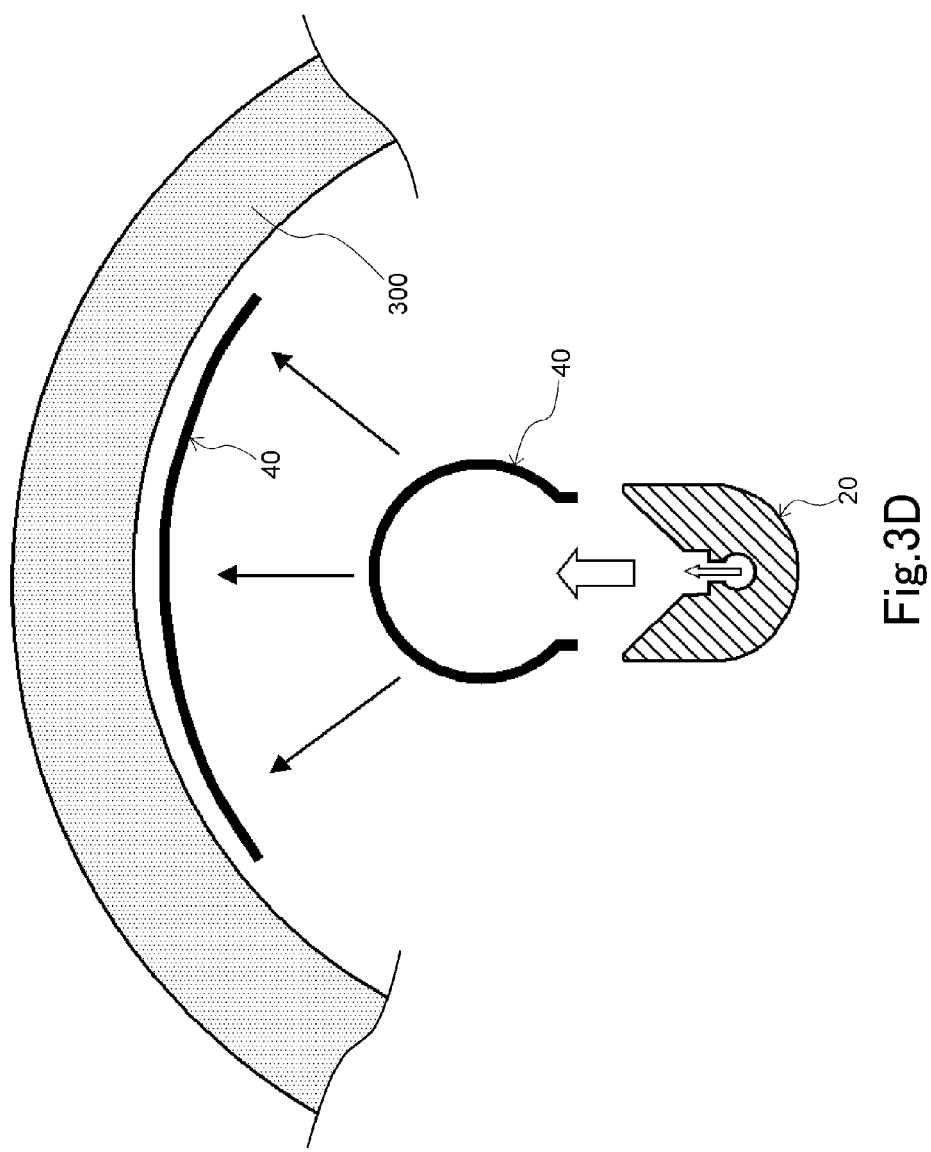

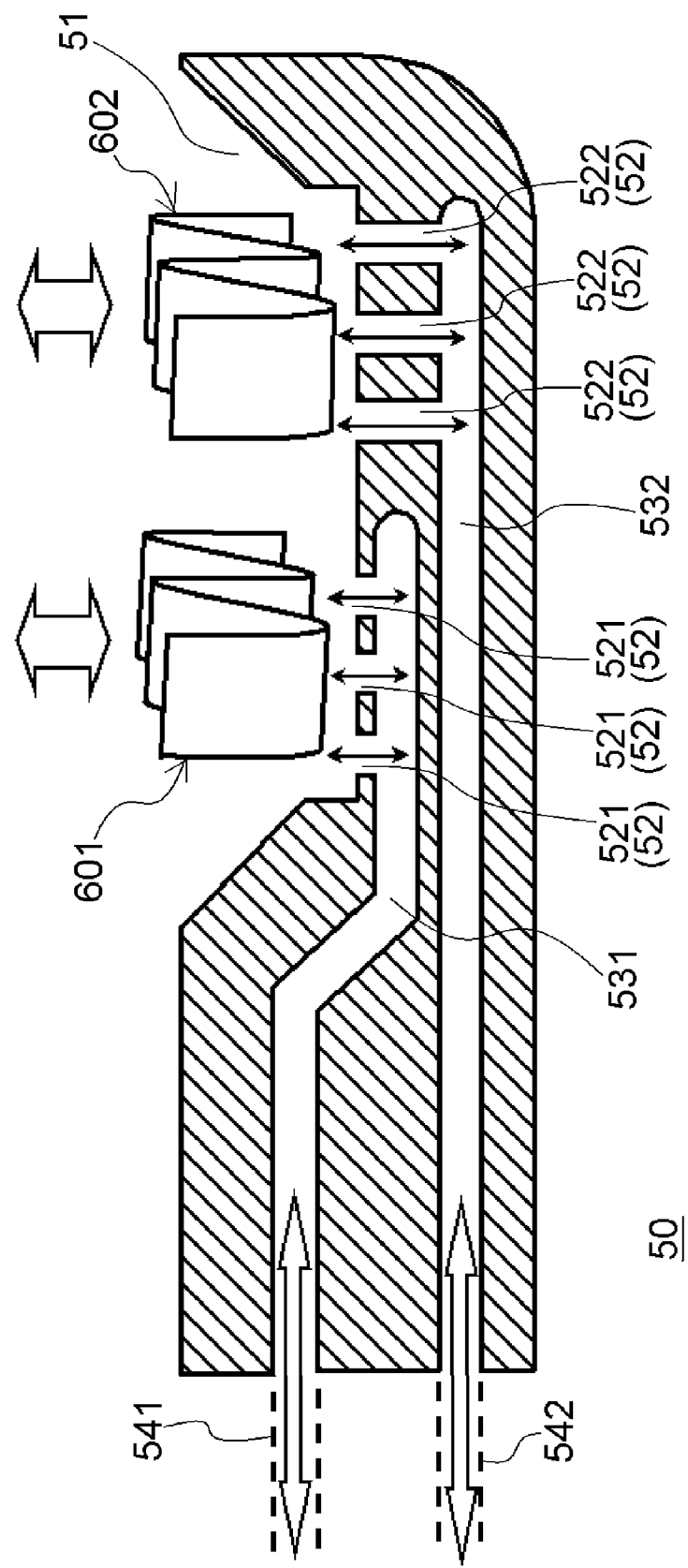

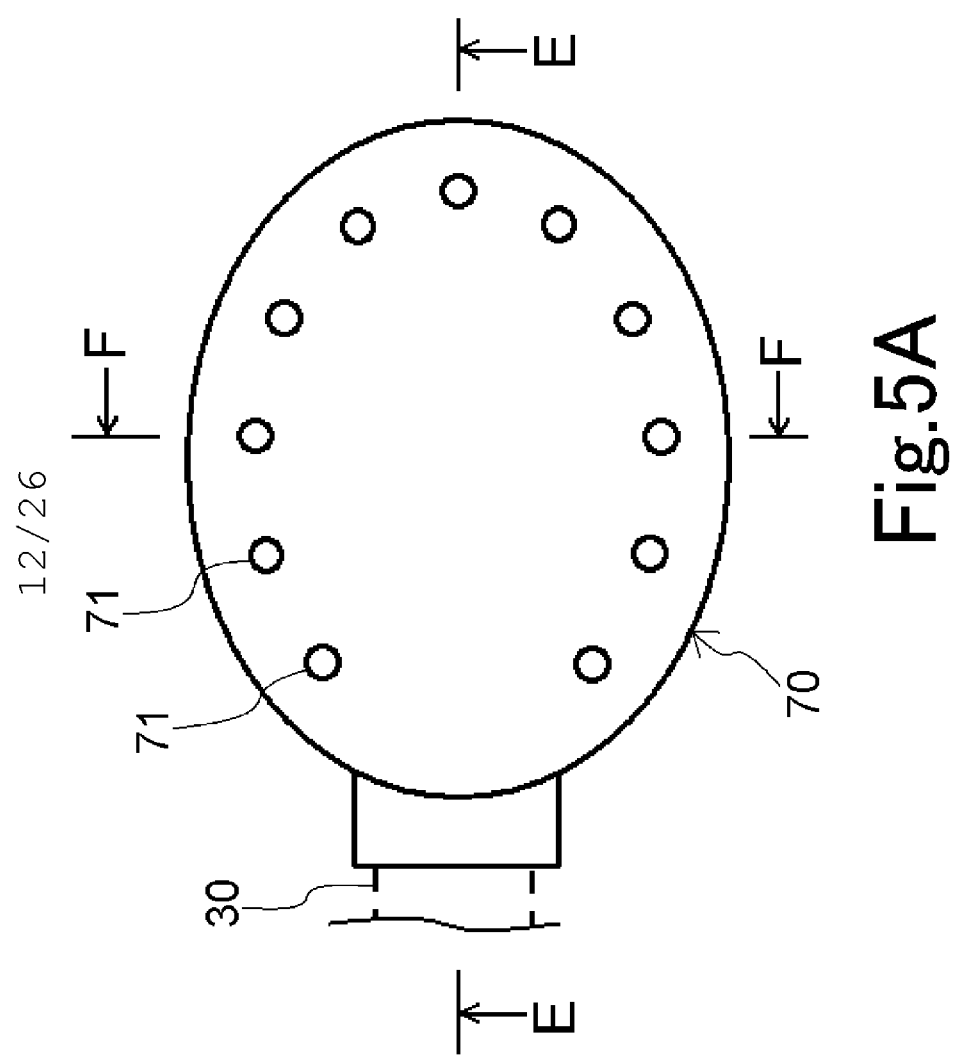

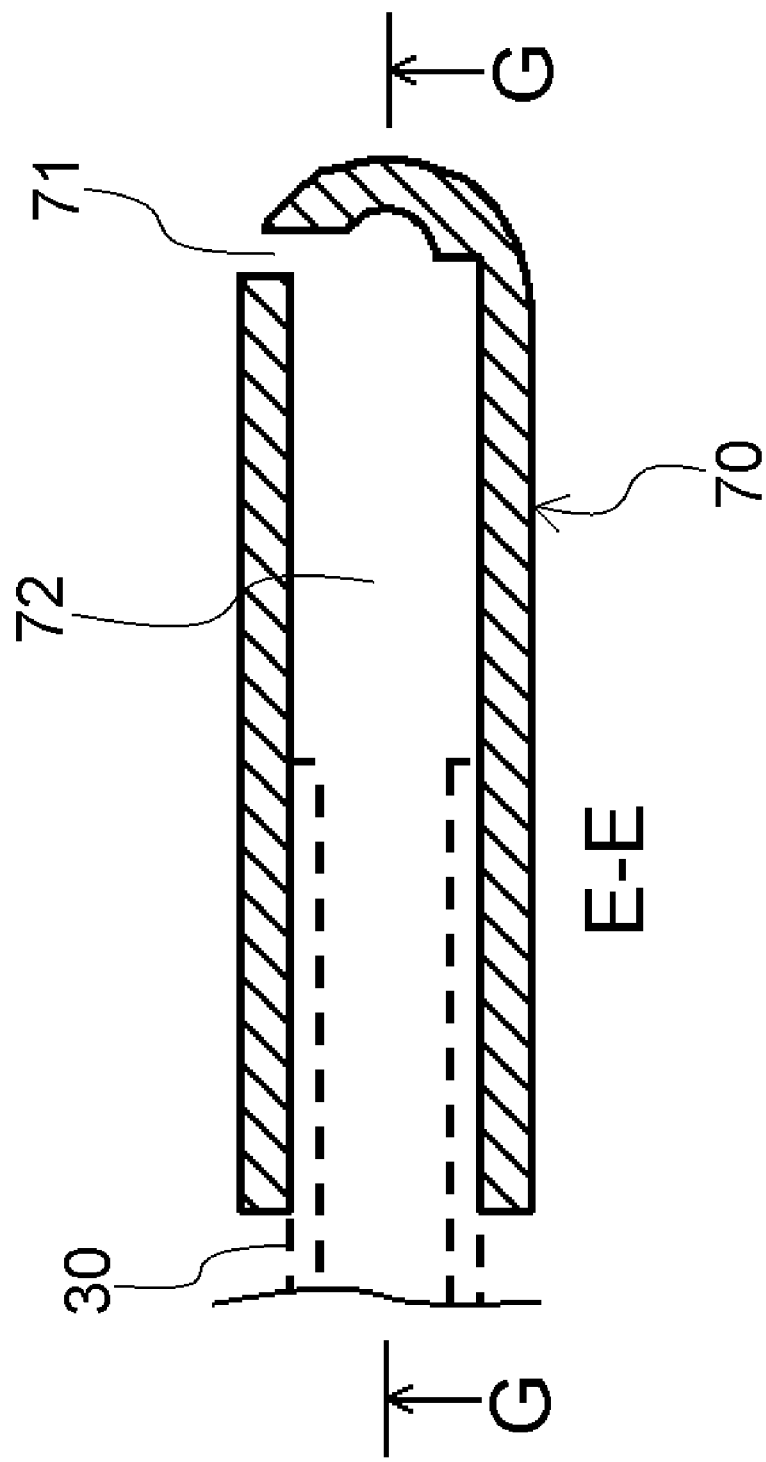

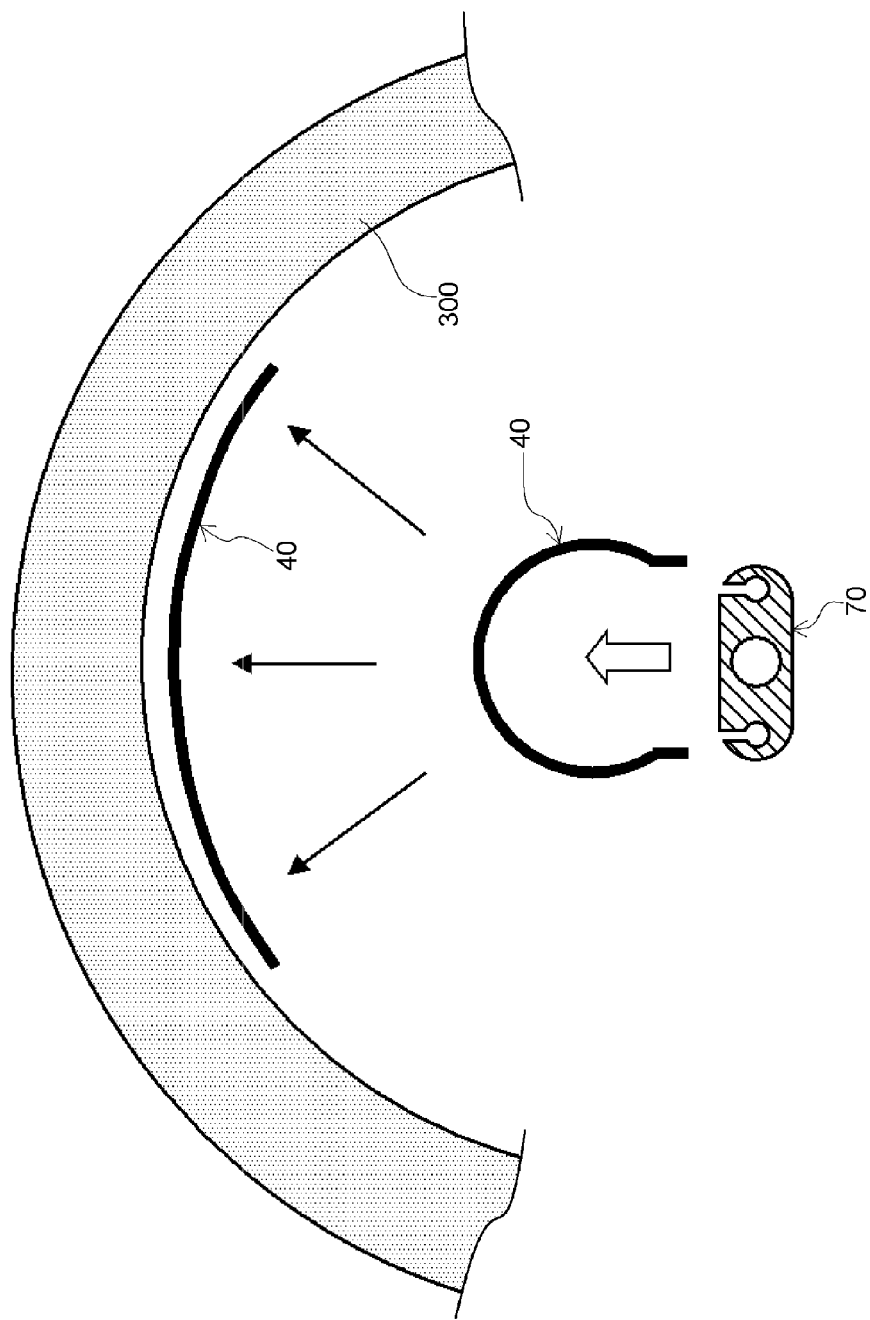

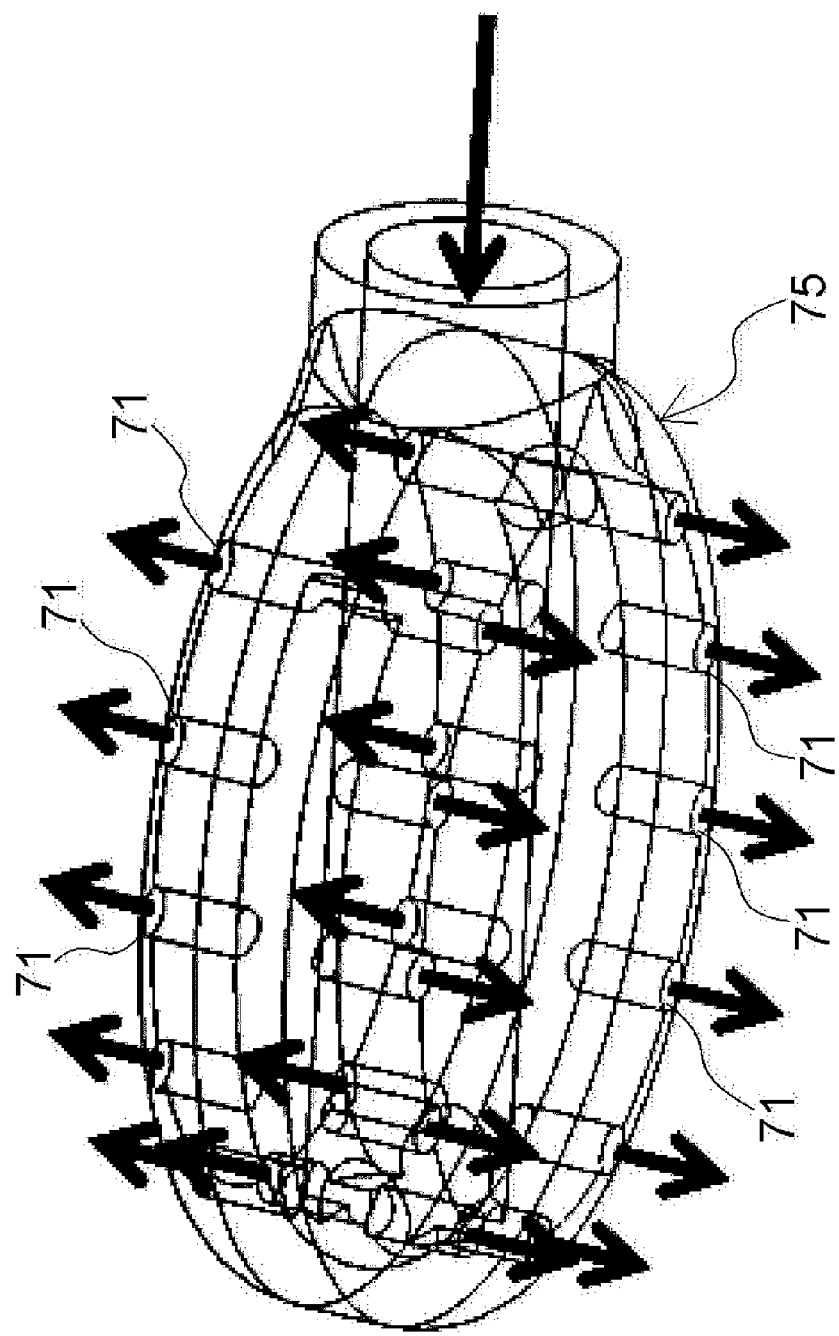

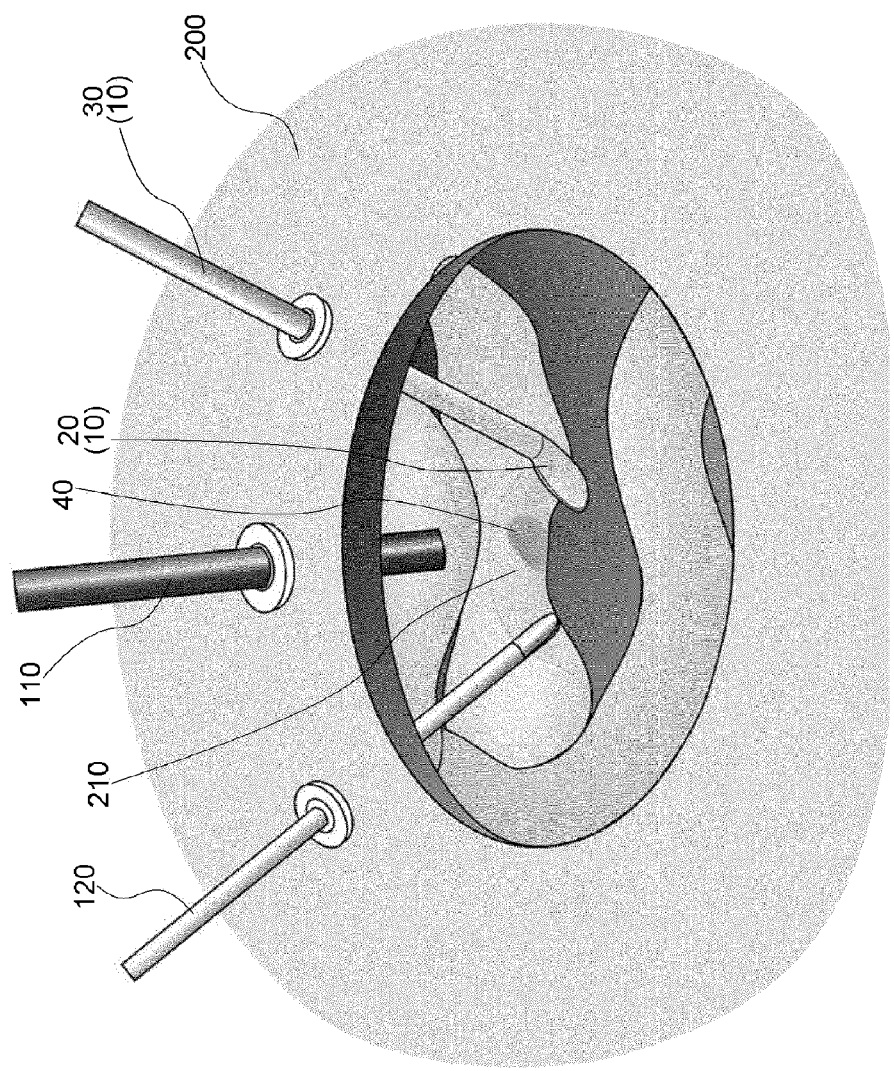

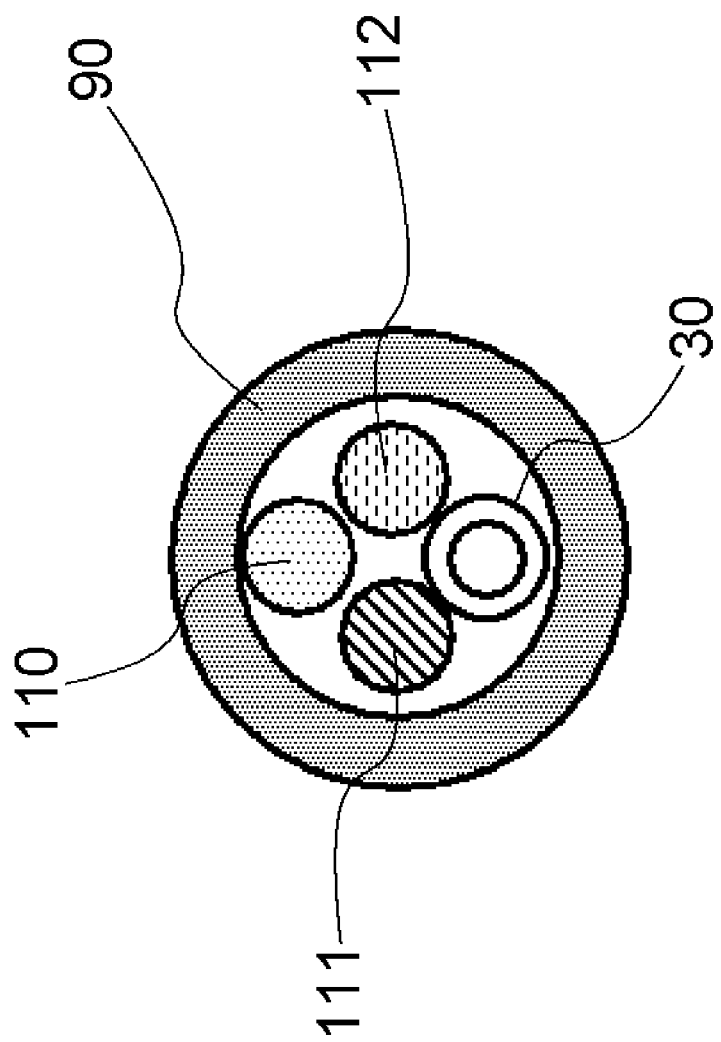

SHEET SHAPED THERAPEUTIC SUBSTANCE TRANSFER APPARATUS AND METHOD OF AFFIXING SHEET SHAPED THERAPEUTIC SUBSTANCE

CROSS-REFERENCE TO RELATED APPLICATIONS

The present invention is a 35 U.S.C. 371 National Stage Entry of PCT/JP2013/078645, filed Oct. 23, 2013, which claims priority from Japanese Patent Application No. 2012-240774, filed on Oct. 31, 2012, the contents of both of which are herein incorporated by reference in their entirety.

TECHNICAL FIELD

The present invention relates to a sheet shaped therapeutic substance (a cell sheet or the like) transfer apparatus for use in transferring a therapeutic substance, formed in a sheet shape, for application.

BACKGROUND OF THE INVENTION

Therapeutic methods have been known in which a substance (a sheet shaped therapeutic substance), formed in a thin sheet shape, is affixed to an affected area of a patient. As part of a regenerative therapy conducted in recent years, in particular, the therapeutic methods have heretofore been conducted for application of a sheet (a cell sheet) made of an externally cultured cell. For the sake of executing such therapeutic methods, the cell sheet needs to be transferred to the affected area and accurately applied thereto. There is also likelihood in some cases that the affected area belongs to the inside (such as digestive organs) of a human body. In such likelihood, the cell sheet needs to be transferred toward the inside of the human body and carry out work for affixing the cell sheet to the affected area while observing the same from the outside. This results in need to use a dedicated device.

Patent Document 1 describes about an apparatus including a head, mounted on a distal end of a syringe, which has a distal end formed with a holding surface on which a sheet shaped substance is held in place. The holding surface has small apertures that are filled with liquid, which is depressurized such that the sheet shaped substance is adsorbed onto the holding surface. Manipulating the syringe enables controls to be performed for depressurizing or pressurizing liquid. Liquid may suffice to be depressurized for transfer of the sheet shaped substance and pressurized for affixing step.

Patent Document 2 describes about an apparatus including a sheet supporting body (head) available to be switched between two kinds of planar and cylindrical shapes. The sheet supporting body also includes an opening portion and depressurizing air in the opening portion allows a sheet shaped substance to be adsorbed. With the sheet supporting body made cylindrical in shape during transfer, further, the whole of the sheet can be accommodated in a tube for enabling the sheet shaped substance to be protected. Also, this makes it possible to easily transfer the sheet supporting body into the living body. When mounting the sheet shaped substance or when affixing the same, the sheet shaped substance is made planar in shape, resulting in a capability of easily performing such works.

Patent Document 3 describes about an apparatus in which a balloon, adapted to inflate with internal air being pressurized, is incorporated in a part of an outer tube to allow a sheet shaped substance to be adsorbed onto a surface of the balloon. With such a structure, the sheet shaped substance is adsorbed onto the surface of the balloon with the balloon being deflated, enabling the outer tube to be inserted to the human body. Subsequently, the balloon is moved to a location in close proximity to an affected area, under which the balloon is inflated. This allows the sheet shaped substance to move in a direction perpendicular to an extending direction of the outer tube, thereby enabling the sheet shaped substance to be affixed to the affected area. In this case, since an endoscope or the like can also be incorporated in the outer tube at the same time, it becomes possible to conduct work for application of the sheet shaped substance while observing such work with the endoscope.

By using such apparatuses, it is capable of accurately and safely perform works for transferring the sheet shaped substance, such as the cell sheet or the like, to the affected area and affixing the same thereto.

CITATION LIST

Patent Literature

Patent Document 1: Japanese Patent Provisional Publication No. 2010-82026
Patent Document 2: Japanese Patent Provisional Publication No. 2008-173333
Patent Document 3: Japanese Patent Provisional Publication No. 2008-79783

DISCLOSURE OF THE INVENTION

Problems to be Solved by the Invention

However, although the apparatus described in Patent Document 1 is effective for the sheet shaped substance to be affixed to, for instance, a surface of the human body, the whole structure becomes large in size. Thus, it is apparent that such apparatuses are unsuitable for work to accurately affix the sheet onto a fine area inside the human body. Especially when using the sheet shaped substance of a large surface area, the head also needs to have a distal end portion with an increased surface area and, hence, the distal end portion is enlarged in size. It is thus difficult to insert the apparatus of such a configuration into, for instance, the digestive organs.

The apparatus described in Patent Document 2 has a structure configured to be more easily inserted to the inside of the human body as compared to the apparatus described in Patent Document 1. However, this needs a mechanism for deforming the sheet supporting body, resulting in a complicated structure in an area around the sheet supporting body. After all, it is difficult to miniaturize such an apparatus as a whole and it was difficult to use such an apparatus for performing work of affixing the sheet shaped substance to the inside of the human body.

Although the apparatus described in Patent Document 3 is advantageous in view of a capability of easily performing work inside the human body and particularly effective in view of a capability of performing work while observing the affected area with the use of the endoscope at the same time. Once, for instance, the balloon is inflated, however, a visual field of the endoscope is interrupted. In actual practice, this makes it difficult to perform affixing work while observing the affected area with the use of the endoscope.

With the apparatuses described in Patent Documents 1 and 2, further, the sheet shaped substance is brought into contact with the affected area. Subsequently, liquid or air is pressurized inside the head (sheet supporting body), thereby causing the sheet shaped substance and the head to be separated from each other. With the apparatus described in Patent Document 3, the balloon is inflated to cause the sheet shaped substance to be brought into contact with and affixed to the affected area. Thereafter, the balloon is deflated such that the balloon and the sheet shaped substance are separated from one another.

In actual practice, however, a high adhesion effect exists between the sheet shaped substance, such as the cell sheets, and the head, the sheet supporting body and the balloon or the like. With the use of such an apparatus, therefore, when the sheet shaped substance and the affected area are held in contact with each other, one surface of the sheet shaped substance, facing in opposition to the other surface held in contact with the affected area, still remains in contact with the head, the sheet supporting body and the balloon or the like. Therefore, it was uneasy for the sheet shaped substance to be separated from the head, the sheet supporting body and the balloon after the sheet shaped substance has been affixed to the affected area. In addition, it was much more likely that the sheet shaped substance was broken when the sheet shaped substance was separated from the head, the sheet supporting body and the balloon.

That is, it was difficult to accurately affix the sheet shaped substance to the inside of the human body.

The present invention has been completed in view of the above issues and it is an object to provide an invention to address such issues.

Means for Solving the Problems

The present invention has a structure, as described below, with a view to addressing the above issues.

According to the present invention, there is provided a sheet shaped therapeutic substance transfer apparatus used for holding a sheet shaped therapeutic substance on a head and subsequently affixing the sheet shaped therapeutic substance onto an affected area, including: a vent pipe connected to the head and internally storing fluid; wherein the head has a surface formed in a convex shape, and a plurality of vent apertures to eject the fluid in a direction approximately perpendicular to a longitudinal direction of the vent pipe, is formed in the surface, the sheet shaped therapeutic substance is adsorbed in the surface such that the sheet shaped therapeutic substance is held when a pressure of the fluid is made negative, and the adsorbed sheet shaped therapeutic substance is removed and blown off from the head when the pressure of the fluid is made positive.

With the sheet shaped therapeutic substance transfer apparatus according to the present invention, the head includes two surfaces configured in the convex shapes, and the plurality of vent apertures, formed in each of the surfaces, include vent aperture groups each associated with each of the surfaces; and flow channels of the fluid are provided in the vent pipe and the head, so that each of the flow channels corresponds to each of the vent aperture groups independently.

According to the present invention, there is provided a sheet shaped therapeutic substance transfer apparatus used for holding a sheet shaped therapeutic substance on a head and subsequently affixing the sheet shaped therapeutic substance onto an affected area, including: a vent pipe connected to the head and internally storing fluid; wherein the head has a concave portion in a surface, and a plurality of vent apertures to eject the fluid in a direction approximately perpendicular to a longitudinal direction of the vent pipe, is formed in the concave portion, the sheet shaped therapeutic substance is adsorbed in the surface such that the sheet shaped therapeutic substance is held when a pressure of the fluid is made negative, and the adsorbed sheet shaped therapeutic substance is removed and blown off from the head when the pressure of the fluid is made positive.

With the sheet shaped therapeutic substance transfer apparatus according to the present invention, the plurality of vent apertures is classified into a plurality of vent aperture groups each having the plurality of vent apertures; flow channels of the fluid are provided in the vent pipe and the head, so that each of the flow channels corresponds to each of the vent aperture groups independently.

The sheet shaped therapeutic substance transfer apparatus according to the present invention further includes an endoscope having a distal end enabling the affected area to be visually observed, and movable approximately in parallel to the vent pipe; both of the head and the endoscope being incorporated in an outer tube section and having distal ends exposed from one end of the outer tube section.

According to the present invention, there is provided a method of affixing a sheet shaped therapeutic substance using the sheet shaped therapeutic substance transfer apparatus, the method including: locating the head in a position in which an area for the sheet shaped therapeutic substance to be affixed and the sheet shaped therapeutic substance held by the head are close proximity to each other with the sheet shaped therapeutic substance being held by the head; and making a pressure of fluid positive for causing the sheet shaped therapeutic substance to be removed and blown off from the head for affixing the sheet shaped therapeutic substance to the area for the sheet shaped therapeutic substance to be affixed.

With the method of affixing the sheet shaped therapeutic substance according to the present invention, when holding the sheet shaped therapeutic substance on the head, the sheet shaped therapeutic substance is adsorbed by the vent apertures under a folded state.

With the method of affixing the sheet shaped therapeutic substance according to the present invention, the sheet shaped therapeutic substance transfer apparatus is used with an endoscope in combination.

Effect of the Invention

With the present invention configured in such a structure set forth above, the sheet shaped therapeutic substance can be accurately and easily affixed to the inside of the human body.

BRIEF DESCRIPTION OF THE DRAWINGS

FIGS. 1A and 1B are top view and a side view showing a structure of a sheet shaped therapeutic substance transfer apparatus of a first embodiment according to the present invention.

FIGS. 2A, 2B, 2C and 2D are cross-sectional views taken on line A-A, B-B, C-C and D-D, respectively, showing a structure of a head used in the sheet shaped therapeutic substance transfer apparatus of the first embodiment according to the present invention.

FIGS. 3A, 3B, 3C and 3D are views for typically showing how a sheet shaped therapeutic substance is affixed with the use of the sheet shaped therapeutic substance transfer apparatus of the first embodiment according to the present invention.

FIG. 4 is a cross-sectional view showing a first modified form of the head used in the sheet shaped therapeutic substance transfer apparatus of the first embodiment according to the present invention.

FIGS. 5A, 5B, 5C and 5D represent a top view and cross-sectional views (taken on lines E-E, F-F and G-G, respectively) for typically showing a second modified form of the head used in the sheet shaped therapeutic substance transfer apparatus of the first embodiment according to the present invention.

FIGS. 6A and 6B are views for typically showing how the sheet shaped therapeutic substance is affixed by utilizing the second modified form of the head used in the sheet shaped therapeutic substance transfer apparatus of the first embodiment according to the present invention.

FIG. 7 is a perspective view showing a structure of a third modified form of the head used in the sheet shaped therapeutic substance transfer apparatus of the first embodiment according to the present invention.

FIG. 8 is a view for typically showing how the sheet shaped therapeutic substance is affixed to the inside of a human body by using the sheet shaped therapeutic substance transfer apparatus of the first embodiment according to the present invention.

FIG. 12 is a cross-sectional view of a modified form of the sheet shaped therapeutic substance transfer apparatus of the second embodiment according to the present invention.

BEST MODE FOR CARRYING OUT THE INVENTION

Now, a sheet shaped therapeutic substance transfer apparatus of an embodiment according to the present invention will be described below. The sheet shaped therapeutic substance transfer apparatus is capable of adsorbing and holding a sheet shaped substance (such as a cell sheet or the like) and transferring the same. Subsequently, the sheet shaped therapeutic substance can be affixed to a desired target region (such as an affected area or the like) of a living body. When this takes place, even if such a place belongs to the inside (digestive organs or the like) of the human body, relevant work can be performed accurately in safe.

With such a sheet shaped therapeutic substance transfer apparatus, the sheet shaped substance is adsorbed onto a head by means of negative pressure in the same manner as that achieved by the apparatuses described in Patent Documents 1 and 2. However, the head has a surface, onto which the sheet shaped substance is adsorbed, which is not formed in a planar shape but formed in concave or convex shapes. Further, a plurality of vent apertures in which fluid (gas or liquid) pressure is reduced to adsorb the sheet shaped substance is formed on the surface. To this end, a vent pipe is connected to the head for internally storing fluid. The pressure of fluid can be controlled in a place (i.e., for instance, an area outside the human body when the sheet shaped substance is affixed to the internal part of the human body) far from the head.

Further, the head has a plurality of vent apertures for ejecting fluid in a direction substantially perpendicular to a longitudinal axis of the vent pipe. When applying the sheet shaped substance, furthermore, the sheet shaped substance is preferably kept in a non-contact state with a region (affected area) for the sheet shaped substance to be affixed. Under such a state, fluid in the vent pipe is pressurized to cause the sheet shaped substance to be blown off from the head in the direction substantially perpendicular to the longitudinal axis of the vent pipe such that the sheet shaped substance is applied. To this end, the sheet shaped therapeutic substance transfer apparatus has the head configured in a shape to easily perform blowing-off.

First Embodiment

Figure 1A:
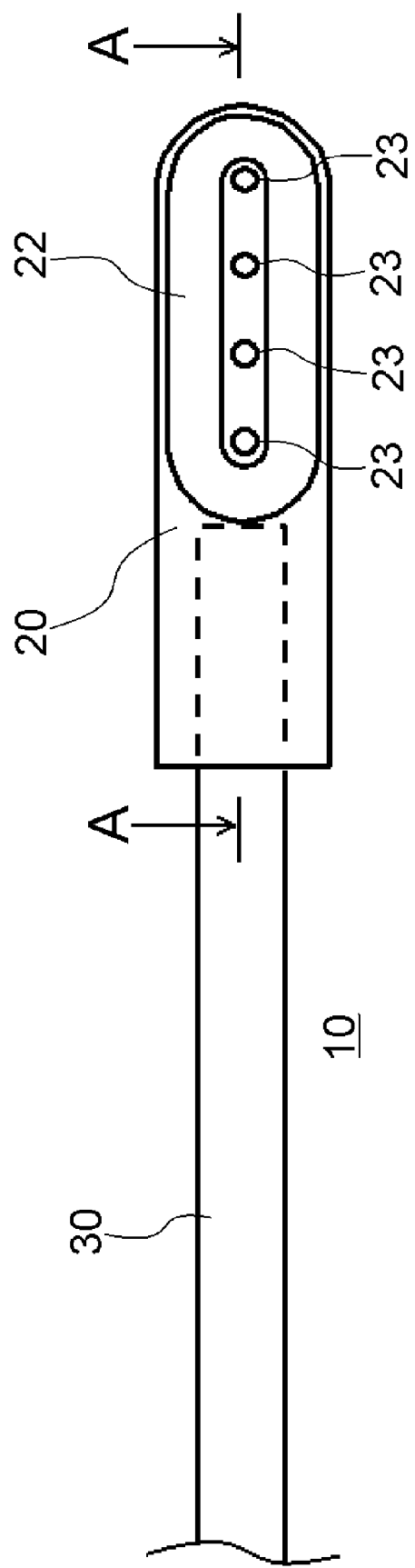
Figure 2B:
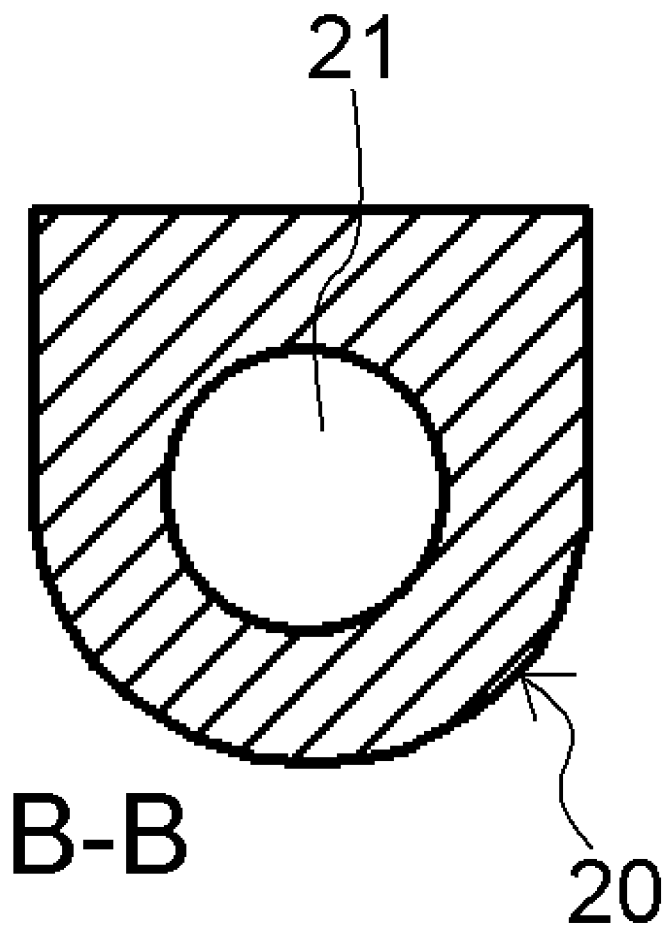
Figure 2C:
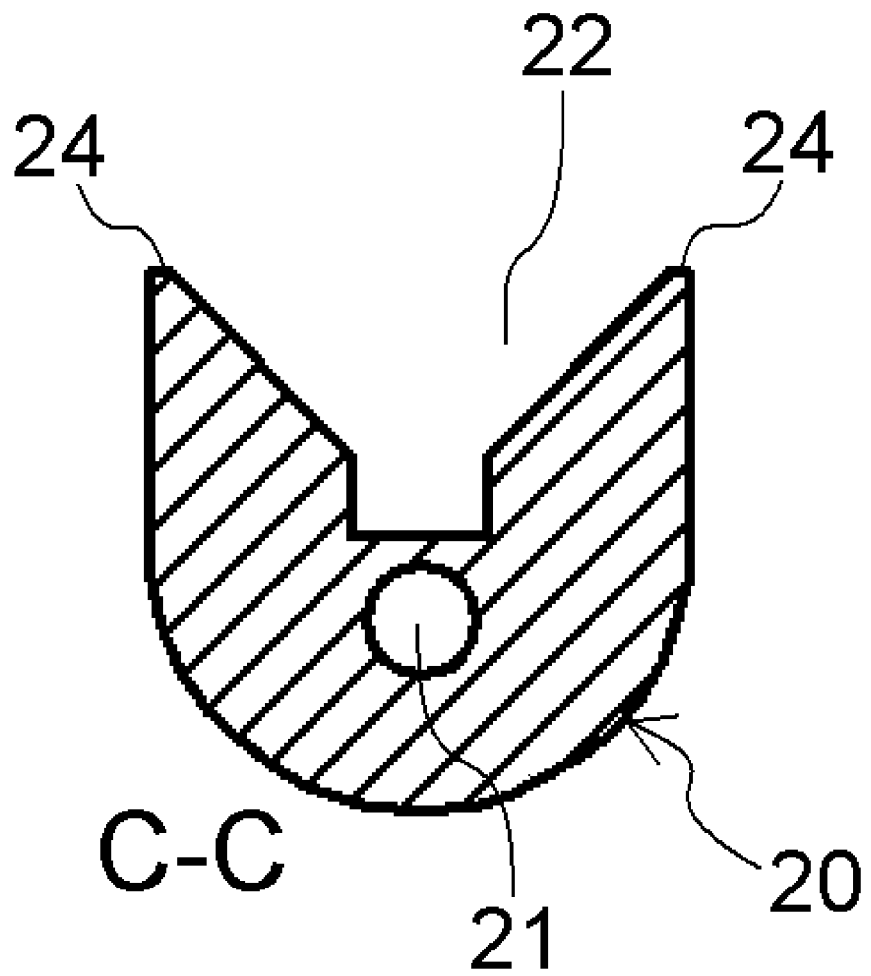
Figure 2D:
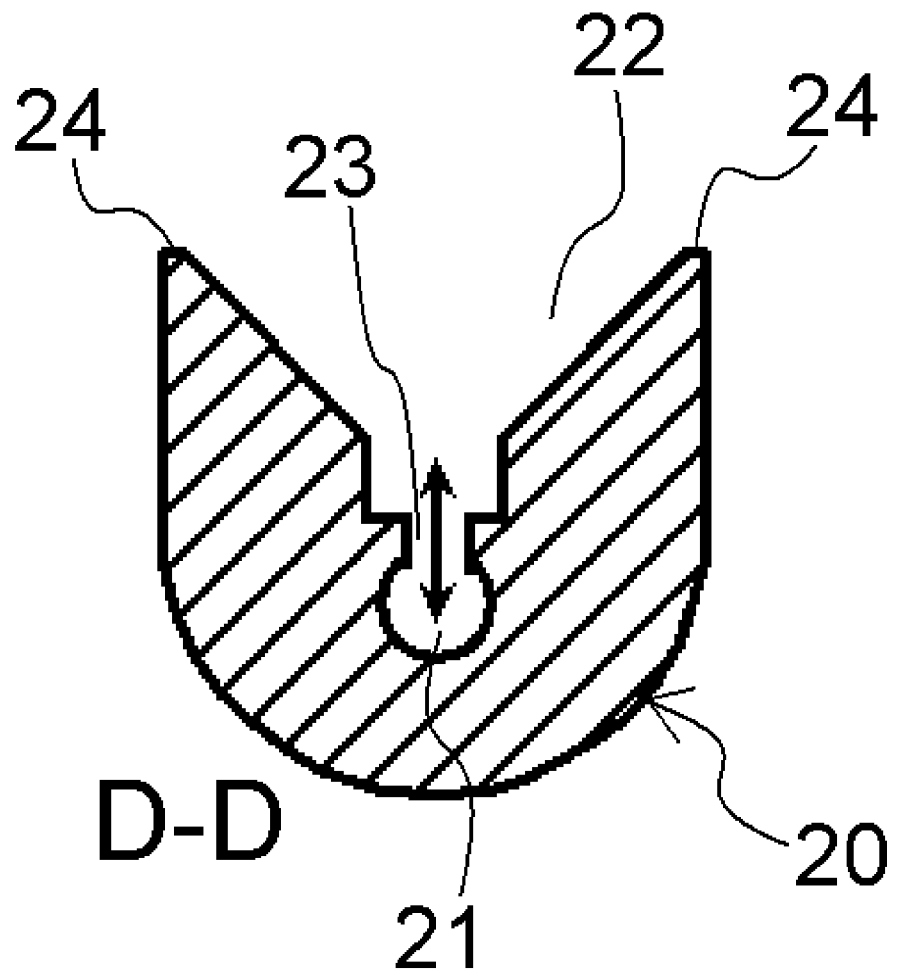

A first embodiment is directed to a sheet shaped therapeutic substance transfer apparatus (hereinafter, abbreviated as a transfer apparatus) which has a function to transfer a sheet shaped substance for application. FIGS. 1A and 1B represent a top view of the transfer apparatus 10 and a side view of the same, respectively. The transfer apparatus 10 includes a head 20 and a vent pipe 30. FIGS. 2A to 2D represent cross-sectional views taken on lines A-A, B-B, C-C and D-D, respectively. The sheet shaped substance is mounted on the head 20 at an upper side thereof.

As shown in FIGS. 1A and 1B, the head 20 is fixedly secured to a right end (one end) of the vent pipe 30. The vent pipe 30 is made tabular in shape in which fluid (such as air) is stored. In FIGS. 1A and 1B, the vent pipe 30 has a left end (other end), extending to an area omitted in figure, to which a pump and a syringe or the like are mounted such that fluid can be depressurized or pressurized in the vent pipe 30. The vent pipe is approximately determined to have a length in an extent to sufficiently cover a distance range from, for instance, the internal part (affected area) of a living body to the pump located outside the living body. Although, in particular, air may be preferably used for the fluid, liquid such as water or physiological salt solution may also be employed.

The vent pipe 30 and the head 20 are connected to and fixedly secured to each other such that fluid is kept in air-tightness. This allows fluid to be introduced into a cavity portion 21 of the head 20. As shown in FIGS. 2A to 2D, an upper surface of the head 20 is not formed in a planar shape but formed with a concave portion 22 that is elongated in a longitudinal direction (left and right direction as viewed in FIGS. 1A and 1B) of the vent pipe 30. The concave portion 22 has a bottom wall formed with four vent apertures 23 arranged in the left and right direction. The vent apertures 23 are connected to the cavity portion 21. When a negative fluid pressure is created inside the vent pipe 30, therefore, the vent apertures 23 allow the concave portion 22 to adsorb the sheet shaped substance for application. In contrast, if a positive fluid pressure is created inside the vent pipe 30, the adsorbed sheet shaped substance can be released. With the head 20 having such a simplified structure, an overall structure can be miniaturized. In particular, the head 20 extends in an elongated direction (longitudinal direction of the vent pipe 30: the left and right direction as viewed in FIGS. 1A and 1B) along which the vent apertures 23 are arranged. However, cross-sectional area or maximum width, perpendicular to the longitudinal direction, can be made. In addition, the head 20 and the vent pipe 30 may be preferably made of polytetrafluoroethylene or the like that is non-toxic to the human body, light weight and easy to be processed.

Cross-sectional area and maximum width of the vent pipe 30 and the head 20, perpendicular to the longitudinal direction(left and right direction as viewed in FIGS. 1A and 1B) of the vent pipe 30, must be small, such that the vent pipe 30 and the head 20 can be inserted to the internal part of the living body easily. For instance, the esophagus of the human body has an inner diameter (the maximum diameter) approximately ranging from 15 to 30 mm (in a relaxing state) at most and is likely to be zeroed in a contracting state. Meanwhile, the sheet shaped substance (a cell sheet or the like) is suitably determined in size, according to a status of the affected area, which is sometimes required to fall in the same value, approximately ranging from 20 to 30 mm, as the inner diameter of the esophagus. In such a case, it is apparent that it becomes difficult to insert a sheet shaped substance, developed in a planar shape with such a size, into the body for application thereto.

Therefore, the head 20 is configured in structure so as to provide an ease of permitting the sheet shaped substance to be folded in a small size in support for insertion to the living body and subsequently developing such a sheet shaped substance for application. To this end, the maximum width of the head 20 perpendicular to the longitudinal direction of the vent pipe 30, is determined to be equal to or less than, for instance, 10 mm. The folded sheet shaped substance is also determined to fall in a size approximately equal to or less than such a value.

Figure 3A:
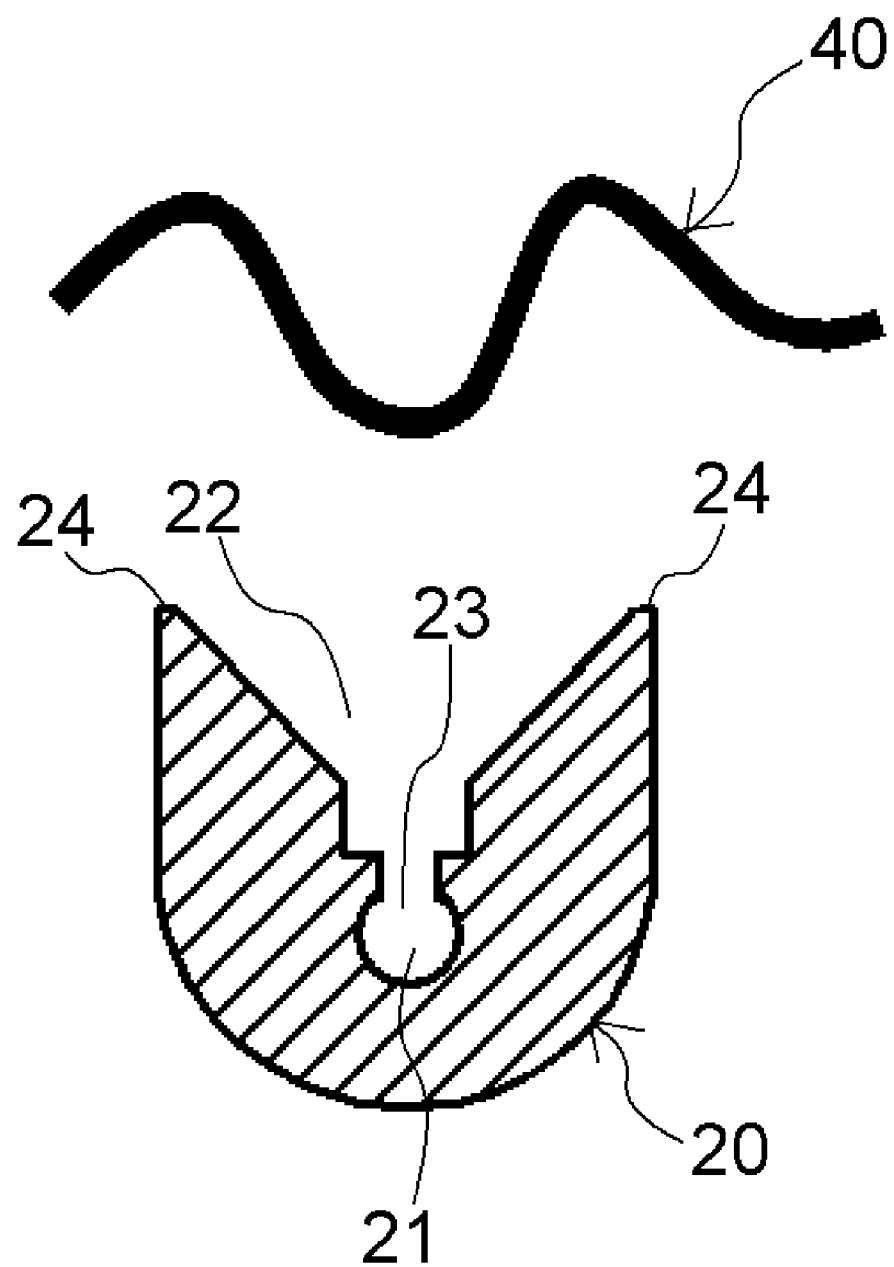
Figure 3B:
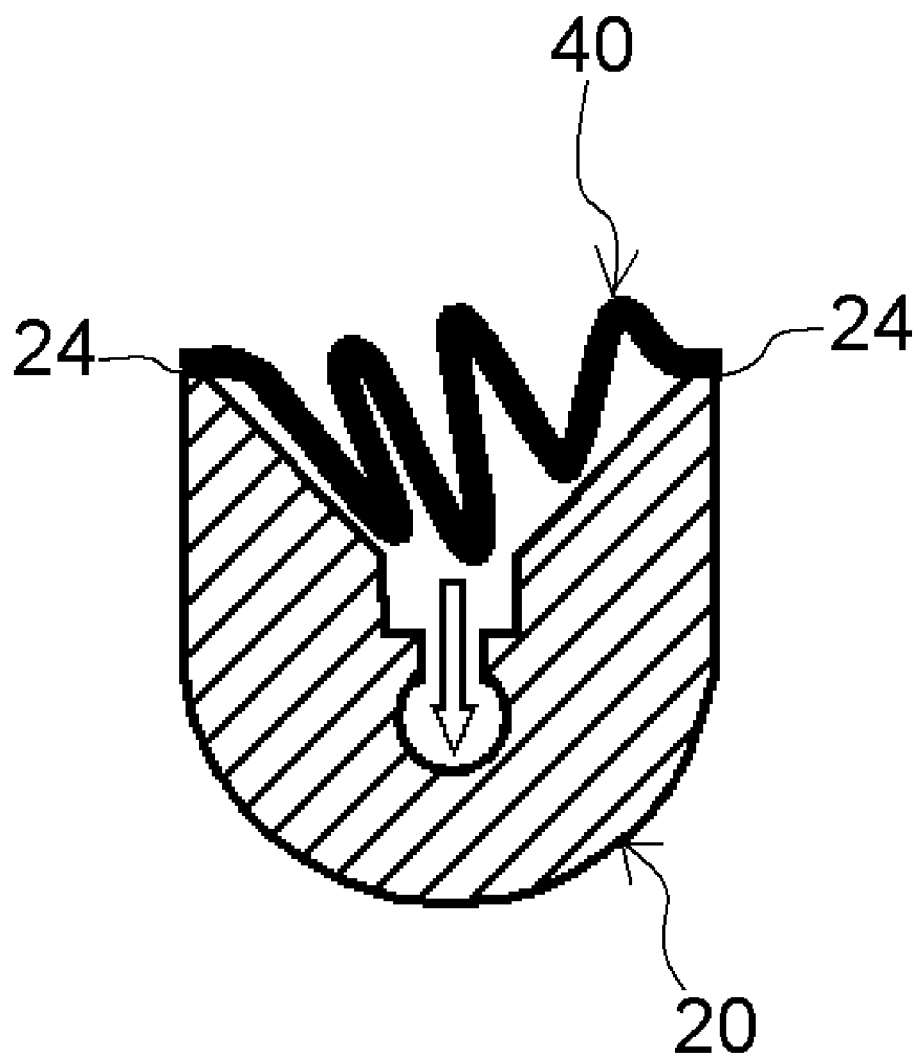
Figure 3C:
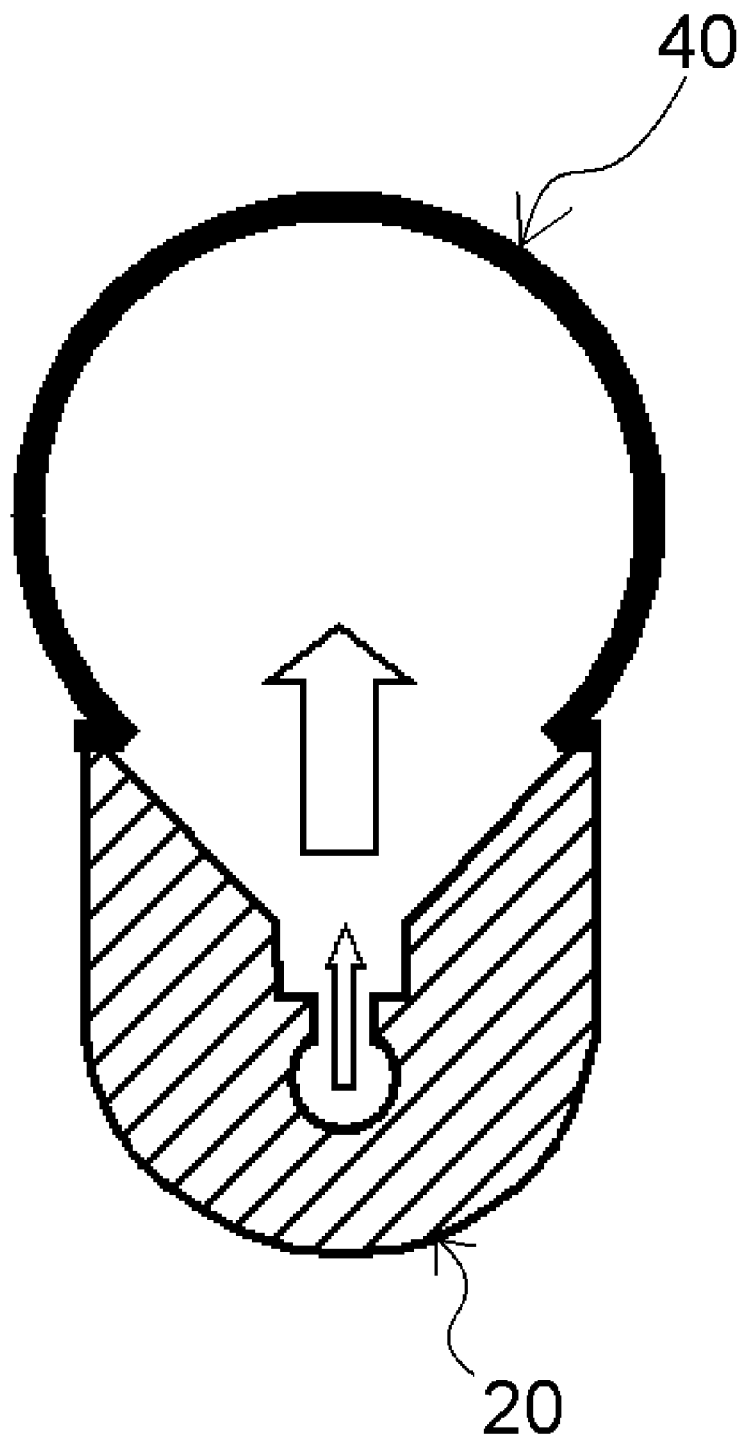

FIGS. 3A to 3C are views typically showing how the sheet shaped substance 40 is mounted on the head 20 and subsequently the resulting sheet shaped substance 40 is removed and blown off. Here, a case is shown in which the sheet shaped substance 40 is applied to the esophagus wall 300. Such a mode is typically shown here in correspondence to FIG. 2D in cross section. As shown in FIG. 3A, here, the sheet shaped substance 40, having a larger size than that of the concave portion 22 or the head 20, is mounted on the head 20. As represented by a cell sheet, the sheet shaped substance 40 to be used here has a high flexibility such that an operator is able to freely fold the same by means of a tweezers or the like.

When the operator mounts the sheet shaped substance 40 on the head 20, therefore, the sheet shaped substance 40 is folded by means of the tweezers or the like and crammed into the concave portion 22 as shown in FIG. 3B. Under such a state, a pressure of the fluid inside the vent pipe 30 is made negative, enabling the sheet shaped substance 40 to be adsorbed by means of the vent apertures 23 in a fixed place. Moreover, this similarly applies to a case in which even though the sheet shaped substance 40 is not intentionally folded by the operator, the sheet shaped substance 40 is mounted with wrinkles being formed. As set forth above, however, a high adhesion effect exists between the sheet shaped substance 40 and the head 20 in general practice and, hence, the sheet shaped substance 40 and the head 20 are fixedly held in close contact with each other over entire contacting areas of these components. For instance, apex portions 24, formed around the concave portion 22 of the head 20 at upper areas thereof, and the sheet shaped substance 40 are also held in close contact with each other. Therefore, it is possible for the sheet shaped substance 40 to be fixedly secured on the transfer apparatus 10 under which the sheet shaped substance 40 can be transferred to the affected area (a region to be affixed: the esophagus wall 300).

Under such a state, the head 20 is moved to an area closer to the region (affected area) for the sheet shaped substance 40 to be affixed. If a pressure of fluid inside the vent pipe 30 is made positive, then, the concave portion 22 is pressurized via the vent apertures 23 formed at the bottom wall of the concave portion 22. In this instance, the sheet shaped substance 40 and the apex portions 24 are held in close contact with each other and pressurized from the vent apertures 23 provided inside the concave portion 22. This allows the sheet shaped substance 40, folded in the concave portion 22, to be brought into an inflated state like a balloon as shown in FIG. 3C. With fluid being further pressurized, the inflated sheet shaped substance 40 is separated and blown off from the head 20 as shown in FIG. 3D. Thereafter, the sheet shaped substance 40, blown off in a widely spread state, can be affixed to the esophagus wall 300.

With the sheet shaped substance 40 mounted on the head 20 in non-contact with the affected area, therefore, by making a pressure of the fluid inside the vent pipe 30 positive, the sheet shaped substance 40 can be removed and can be blown off from the head 20 for application to the affected area. This makes it possible to reliably affix the sheet shaped substance 40 onto the affected area. In addition, examples of the sheet shaped substance 40 may preferably include those of, for instance, multi-layered structures that are preliminarily stacked. In FIGS. 3A to 3C, further, the sheet shaped substance 40 can be folded on the miniaturized head 20 in a compact size as a whole as shown in FIG. 3B. Under such a status, the miniaturized head 20 can pass through the narrow esophagus wall 300. This enables a reduction in a time interval for the sheet shaped substance 40 to pass through the esophagus wall 300 for transfer to the affected area after the sheet shaped substance 40 has been mounted on the head 20.

In FIGS. 3A to 3C, furthermore, the sheet shaped substance 40 has been shown in a mode to be blown off and applied to the affected area after the sheet shaped substance 40 has been brought into a sufficiently inflated state as shown in FIG. 3D. However, the sheet shaped substance 40 may be brought into contact with the affected area under a status where the sheet shaped substance 40 is inflated as shown in FIG. 3C but still remains under a non-blowing-off state. Even under such a circumstance, the sheet shaped substance 40 has an area, opposite to a surface held in contact with the affected area, which is mostly removed from the head 20. Thus, it may be apparent that the sheet shaped substance 40 can be reliably affixed to the affected area in a similar fashion. Alternatively, the affected area and a part of the sheet shaped substance 40 may be held in contact with other before the pressure of the fluid is made positive.

Moreover, the sheet shaped substance 40 can be crammed into the concave portion 22 under the folded state, enabling the sheet shaped substance 40 of a large surface area to be transferred and applied by using the miniaturized head 20. In this instance, no need arises for increasing the cross-sectional area and the maximum width of the head in the direction perpendicular to the longitudinal direction of the vent pipe 30. It is apparent that by setting the region where the vent apertures 23 are arranged wide in the longitudinal direction (left and right direction of FIGS. 1A and 1B) of the vent pipe 30, it is possible to transfer the sheet shaped substance 40 of a wider area. In such a case, for instance, the concave portion 22 may be configured to be slender along the longitudinal direction of the vent pipe 30 with a bottom surface having a further large number of vent apertures formed in arrangement.

In such a case, large flow rate of the fluid through the vent pipe 30 and the concave portion 21 is not needed. The vent pipe 30 and the concave portion 21 may suffice to have conductance to some extents so as to enable the vent apertures 23 to be maintained in negative or positive fluid pressures to realize the operations in FIGS. 3A to 3D. Thus, no need arises for the vent pipe 30 and the concave portion 21 to have increased cross-sectional areas and maximum widths perpendicular to the longitudinal direction of the vent pipe 30. Also, it is unnecessary for the head 20 to have an increased cross-sectional area and maximum width. When using the sheet shaped substance 40 of a large surface area, in addition, the concave portion 22 (head 20) may suffice to be formed in a slender configuration along the extending direction of the vent pipe 30. Even when using the sheet shaped substance 40 of a further wider surface area, therefore, the transfer apparatus 10 can be easily inserted to the human body for usage.

On the contrary, even with the apparatuses described in Patent Documents 1 and 2, it is not impossible for the sheet shaped substance to be blown off in the same manner as that of the transfer apparatus 10 mentioned above. With the apparatuses described in Patent Documents 1 and 2, however, a large head needs to be provided in order to mount the sheet shaped substance of such a large surface area. In particular, this results in an increase in the above-mentioned cross-sectional area and it becomes difficult to insert such a head into the human body.

With the apparatus described in Patent Document 2, further, the sheet supporting body is formed in the cylindrical shape and, in such a case, the apparatus can be miniaturized as a whole, in contrast to a case configured in a planar shape, to minimize the above-mentioned cross-sectional surface area. However, it is necessary to provide not only a ventilation mechanism but also a mechanism for deforming the sheet supporting body in such a shape. This makes it difficult to miniaturize the overall structure after all. When using the sheet shaped substance of the large surface area, therefore, a difficulty is encountered in inserting such an apparatus into the human body for usage. Alternatively, since the sheet shaped substance of the large surface area is held in the planar shape, it is necessary to flow fluid at a large flow rate in order for the sheet shaped substance to be blown off in the same manner as that achieved by the apparatus 10 set forth above. This causes a big vent pipe to be required for accomplishing such a purpose and it becomes difficult to insert the same into the human body for usage.

With the apparatus described in Patent Document 3, as set forth above, it is difficult to accurately affix the sheet shaped substance onto the affected area.

Further, FIG. 4 shows a cross-sectional view of a head 50 representing a first modified form of the head 20 noted above. This cross-sectional view corresponds to FIG. 2A. The head 50 includes a concave portion 51 formed with six vent apertures 52, which are classified into a group of three adjacent first vent apertures 521 and a group of three adjacent second vent apertures 522 (vent aperture groups). All of the first vent apertures 521 are connected to a first cavity portion 531 and all of the second vent apertures 522 are connected to a second cavity portion 532. The first cavity portion 531 is connected to a first vent section 541 and the second cavity portion 532 is connected to a second vent section 542. The first vent section 541 and the second vent section 542 admit fluids under pressures that are individually controlled. To this end, the vent pipe, used in such a case, is provided with flow channels in two systems corresponding to the first vent section 541 and the second vent section 542.

With such a structure, using the two flow channels allows fluids to be independently controlled in pressure for the first vent section 541 and the second vent section 542. This makes it possible to transfer a first sheet shaped substance 601, sucked by the first vent apertures 521, and a second sheet shaped substance 602 sucked by the second vent apertures 522 at the same time. Meanwhile, these substances can be individually affixed by independently creating positive fluid pressures in the first vent section 541 and the second vent section 542, respectively. As set forth above, in addition, no need arises for the first vent apertures 521, the second vent apertures 522 and the associated vent pipes connected to these apertures to have increased cross-sectional areas and maximum widths. This enables the head 50 be formed in a slender configuration along the left and right direction, as viewed in FIG. 4, even in a case where a plurality of vent aperture groups are provided in such a way.

In such a case, the first sheet shaped substance 601 and the second sheet shaped substance 602 may suffice to include those of the same types or of different types. In the former types, for instance, the first sheet shaped substance 601 is affixed to one area and, subsequently, the head 50 is altered to another position in which the second sheet shaped substance 602 can be affixed to a different area. This makes it possible to affix two sheets of the sheet shaped substances of limited surface areas in a wide range. In the latter case, the first sheet shaped substance 601 and the second sheet shaped substance 602 can be laminated and affixed to the same area (affected area) inside the human body.

With the head 50 mentioned above, even in such cases, the plural sheet shaped substances are held in different areas along the longitudinal direction of the vent pipe. Thus, the head 50 has no need to have an increased cross-sectional surface area and maximum width. This makes it easy to insert and use the transfer apparatus into the living body by the use of such a head 50. In the example shown in FIG. 4, moreover, a single concave portion 51 is configured to mount two sheets of sheet shaped substances. However, the concave portions and the vent aperture groups may be preferably provided for the sheet shaped substances, respectively. In addition, the example mentioned above is formed in a configuration enabling the two sheets of sheet shaped substances to be mounted at the same time by using the two groups of vent apertures. However, using more than three vent aperture groups enables the sheet shaped substances of more than three sheets to be mounted at the same time.

While the foregoing description has been made of the example using the head whose surface is formed in the concave portion, on the contrary, such a surface may also be formed in a convex shape. FIGS. 5A to 5D represent a top view of a head 70 of such a configuration, a cross-sectional view taken on line E-E, a cross-sectional view taken on line F-F and a cross-sectional view taken on line G-G, respectively. The head 70 is not formed in the concave portion but entirely formed in a convex portion in an area on which the sheet shaped substance is mounted. Eleven vent apertures 71 are arranged in the vicinity of an outer periphery of the convex portion. The respective vent apertures 71 are connected to an internally formed cavity portion 72, which is connected to the vent pipe 30 in a similar fashion.

Figure 6A:
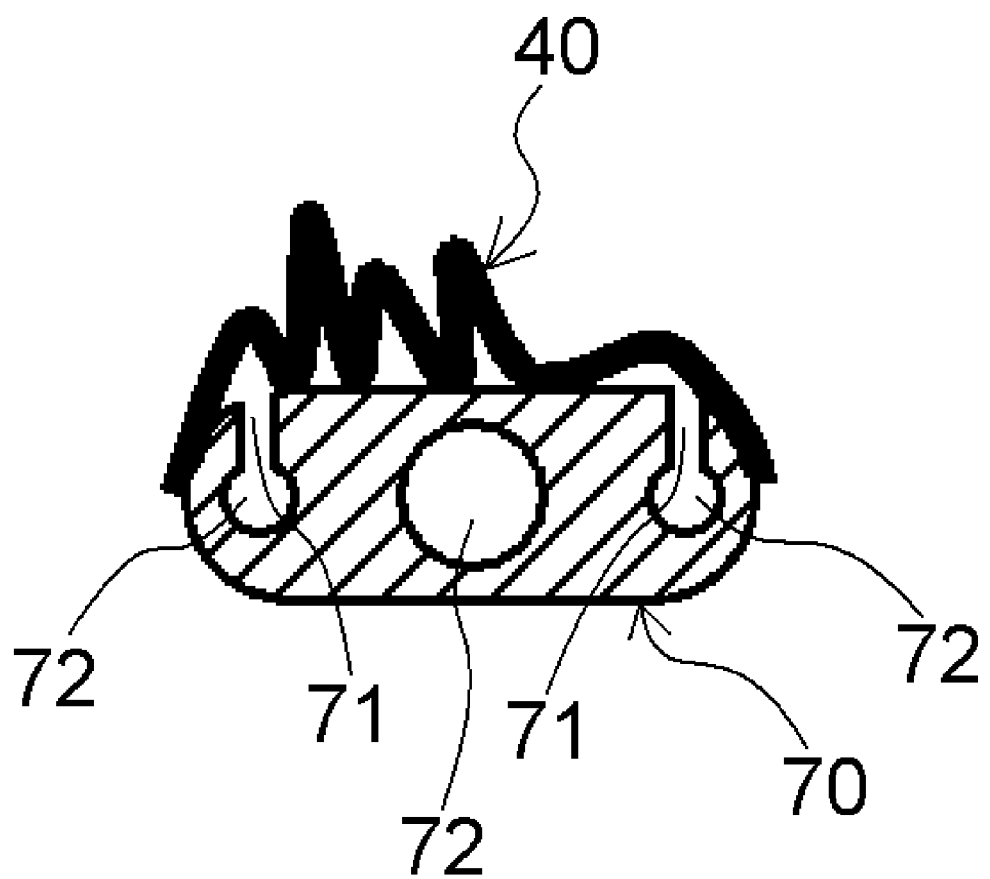

The head 70 has a top side (a side on which the sheet shaped substance is mounted) that is configured in a convex shape. The sheet shaped substance 40 is mounted on the head 70 such that it is covered. Then, by making a pressure of the fluid inside the vent apertures 71 negative, the sheet shaped substance 40 can be transferred. Subsequently, and by making the pressure positive, the sheet shaped substance 40 can be blown off. FIGS. 6A and 6B represent views typically showing such implementations and correspond to FIGS. 3B and 3D, respectively.

Under such circumstances, as shown in FIG. 6A, the sheet shaped substance 40 can be mounted on the head 70 with wrinkles being formed. When this takes place, the sheet shaped substance 40 is held in contact with the outer periphery of the head 70. Then, by making the pressure of the fluid inside the vent apertures 71 positive, the sheet shaped substance 40 can be blown off in the same way as that achieved in the case shown in FIG. 3D. Thus, even though the head 70 is formed in a size larger than those of the heads 20 and 50 in a direction perpendicular to the longitudinal direction of the vent pipe, the head 70 can be used in the same way as those of these heads. However, the surface of the head 70 is configured in the convex shape and this surface is closely parallel to an inner surface of the esophagus wall 300 for the sheet shaped substance 40 to be affixed. Therefore, this particularly makes it possible to perform such applying step (FIG. 6B) in a more reliable fashion.

With the structures shown in FIGS. 5A to 5D and FIGS. 6A and 6B, further, while the vent apertures 71 are provided only on an upper side, the structure may also be configured to allow these apertures to be formed at a lower side. This enables the sheet shaped substances 40 to be mounted on the upper and lower sides such that the sheet shaped substances 40 can be blown off in opposite directions. FIG. 7 is a perspective view for typically showing how fluid flows through the vent apertures 71 for blowing off the sheet shaped substances 40 from a head 75 configured in such a structure. In this case, the vent apertures 71 for the upper side and the vent apertures 71 for the lower side may employ different cavity portions. This enables the sheet shaped substance for the upper side and the sheet shaped substance for the lower side to be individually applied, respectively.

Figure 5C:
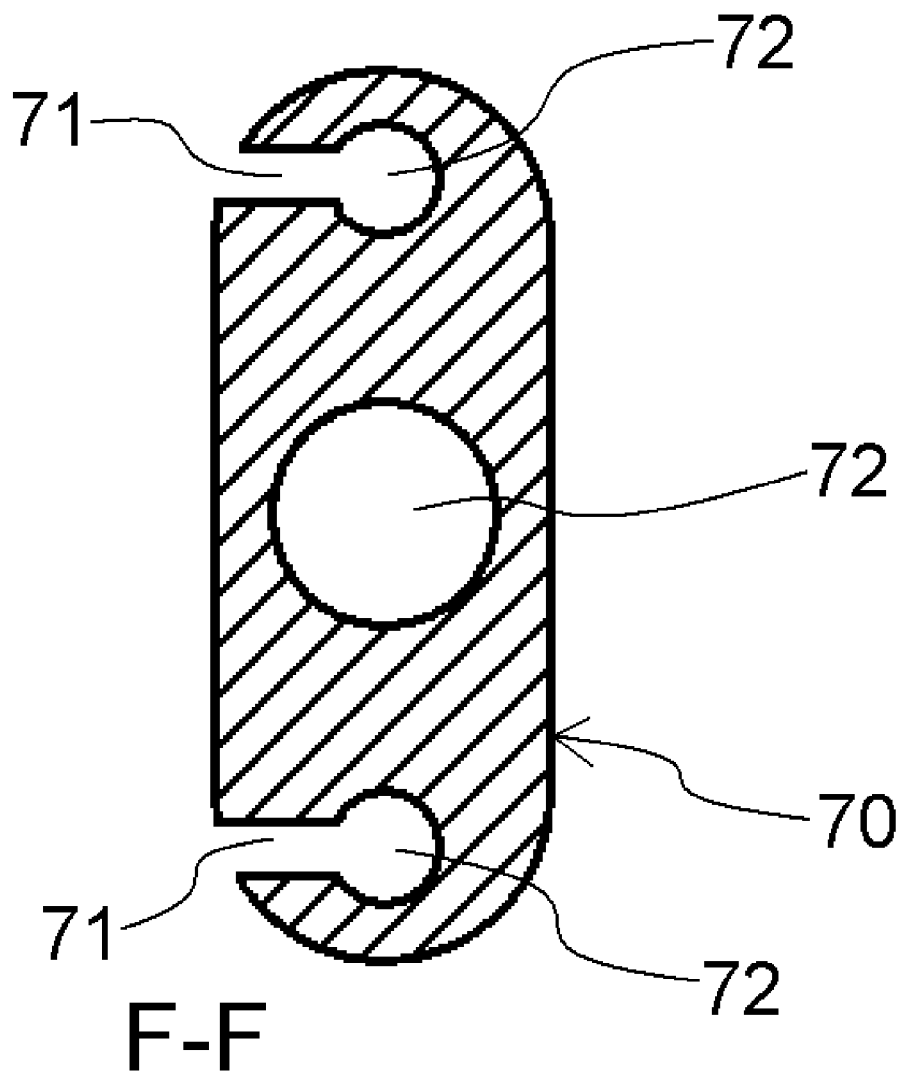
Figure 5D:
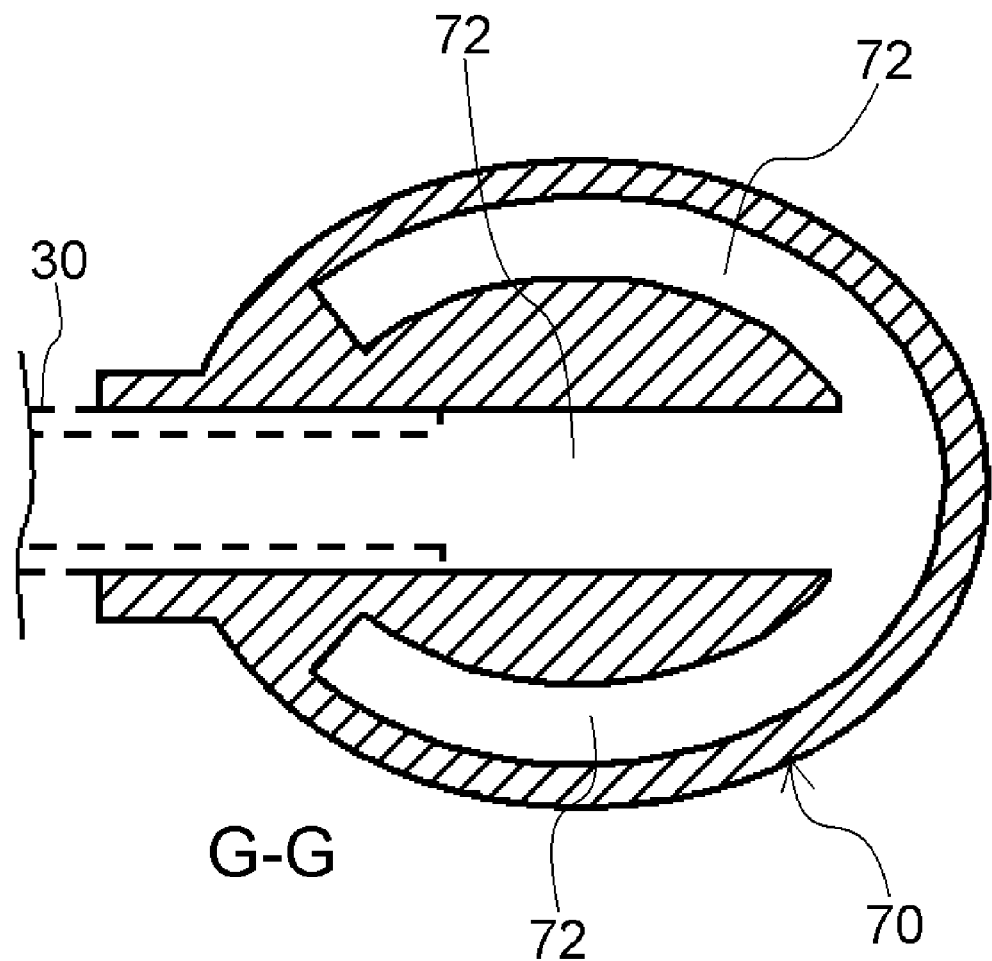

When this takes place, if the vent apertures 71 are arranged in positions near outer circumstantial areas at the upper side and the lower side, respectively, a cavity portion, connected to these apertures, needs to be largely sized as shown in FIG. 5D. If two cavity portions are independently formed, a volume, occupied by such cavity portions inside the head, tends to increase. The heads 20 and 50 are configured in the concave shape, whereas the head 70 (75) is formed in the convex shape as a whole. This results in an increase in volume of a region for the cavity portions to be formed inside the head 70 (75). Thus, it is possible to provide such two cavity portions. That is, with the head having the convex shape, it becomes particularly possible to easily realize a structure for individually mounting the sheet shaped substances on the upper and lower sides.

Furthermore, since the head 70 (75) has no surface formed with a sharp-pointed area, the head can be particularly easy to be inserted to the living body even though such a head is formed in a larger size than those of the heads 20 and 50.

FIG. 8 is a view for typically showing how the sheet shaped substance 40 is affixed to the inside of the living body by using the transfer apparatus 10 mentioned above in actual practice. The transfer apparatus 10, an endoscope 110 and a forceps 120 are inserted through small openings, formed in a living body 200, and extend toward an affected area 210. The endoscope 110 may include an endoscope system integrated with an endoscope in the narrow sense and an associated device such as a lighting equipment or the like. The head 20 of the transfer apparatus 10 is located in proximity to the affected area 210. This enables the affected area 210 to be observed at a distal end of the endoscope 110.

Likewise, the forceps 120, inserted to an area in close proximity to the affected area 210, enables works to be conducted for the affected area 210 and the sheet shaped substance 40 applied thereto. Statuses of such works, a positional relationship between the affected area 210 and the head 20 and a situation of the affixed sheet shaped substance 40 can be observed by using the endoscope 110. The transfer apparatus 10 enables the use of small-sized heads 20, 50 and 70 or the like even when applying the affixed sheet shaped substance 40 of a large surface area. This makes it possible to easily realize the structure of FIG. 8. With such a method, a cell sheet or the like can be affixed to the affected area of the living body in a minimally invasive fashion. In addition, the transfer apparatus 10 and the endoscope (endoscope system) 110 may be inserted through one opening portion (inclusive of an artificially opened area and additionally, for instance, the esophagus, the anus or the like) of the living body.

Figure 9A:
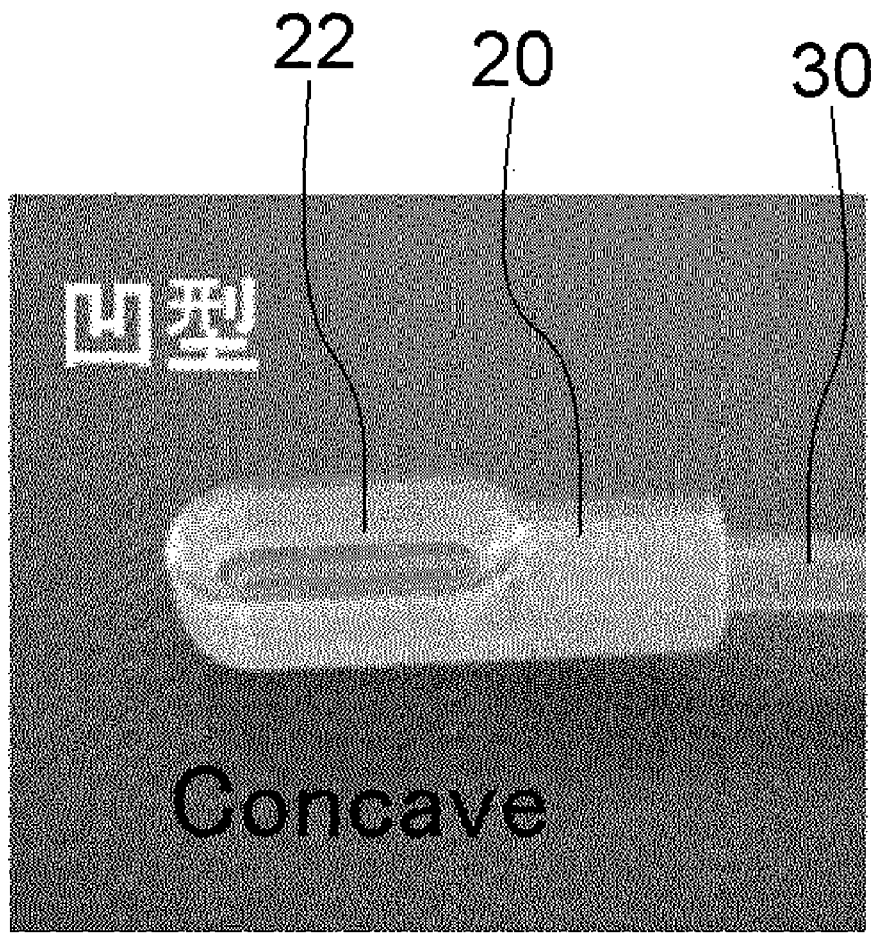
FIGS. 9A and 9B represent photographs of appearances showing the sheet shaped therapeutic substance transfer apparatus according to an example of the present invention and showing how the apparatus is used inside the human body.
Figure 9B:
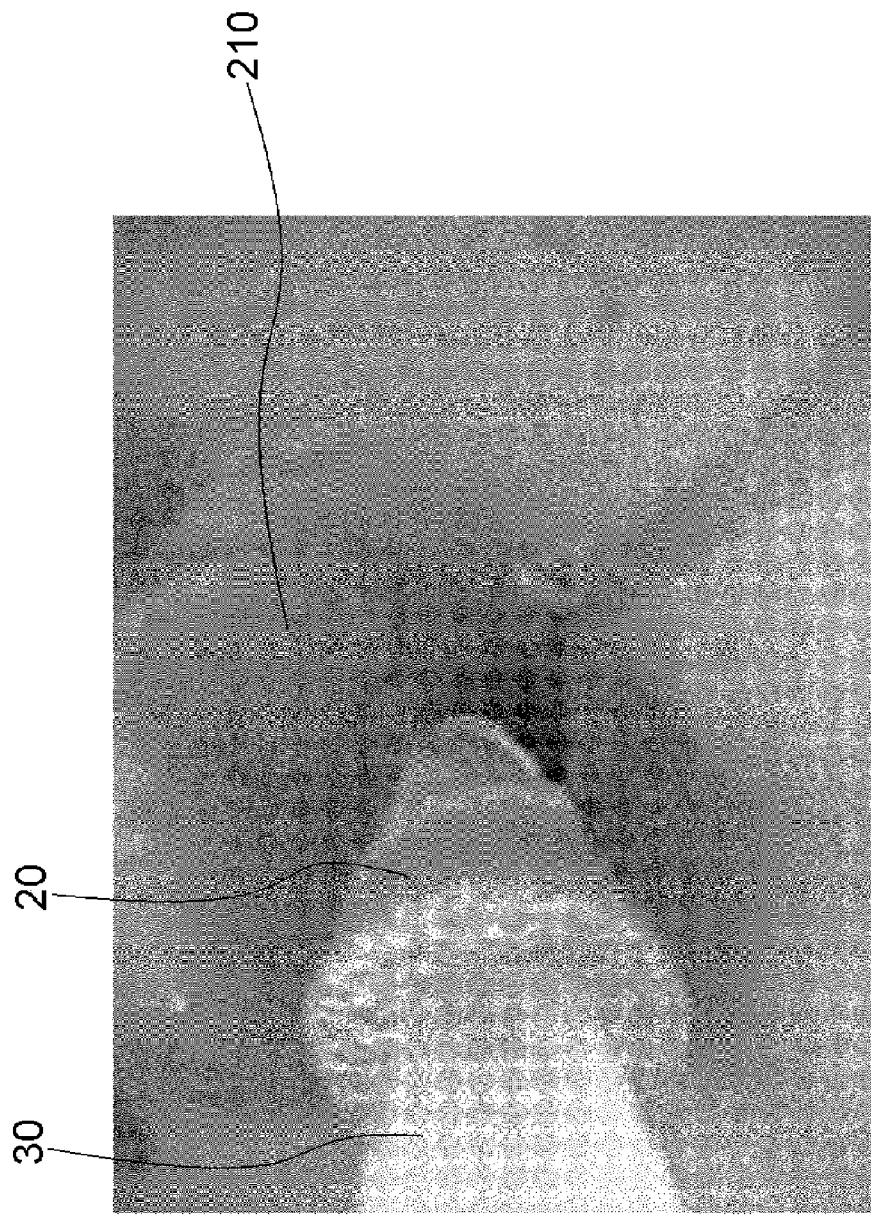

Further, FIGS. 9A and 9B show photographs of the exterior of the transfer apparatus 10 set forth above, and photographs taken when the transfer apparatus is inserted to the digestive organ of the living body for applying the cell sheet thereto. In FIG. 9B, the concave portion 22 or the like of the head 20 can not be seen because the photograph was taken on a side closer to the vent pipe 30. It has been confirmed that such a transfer apparatus can be inserted to the digestive organ and that the cell sheet can be affixed thereto.

Figure 10:
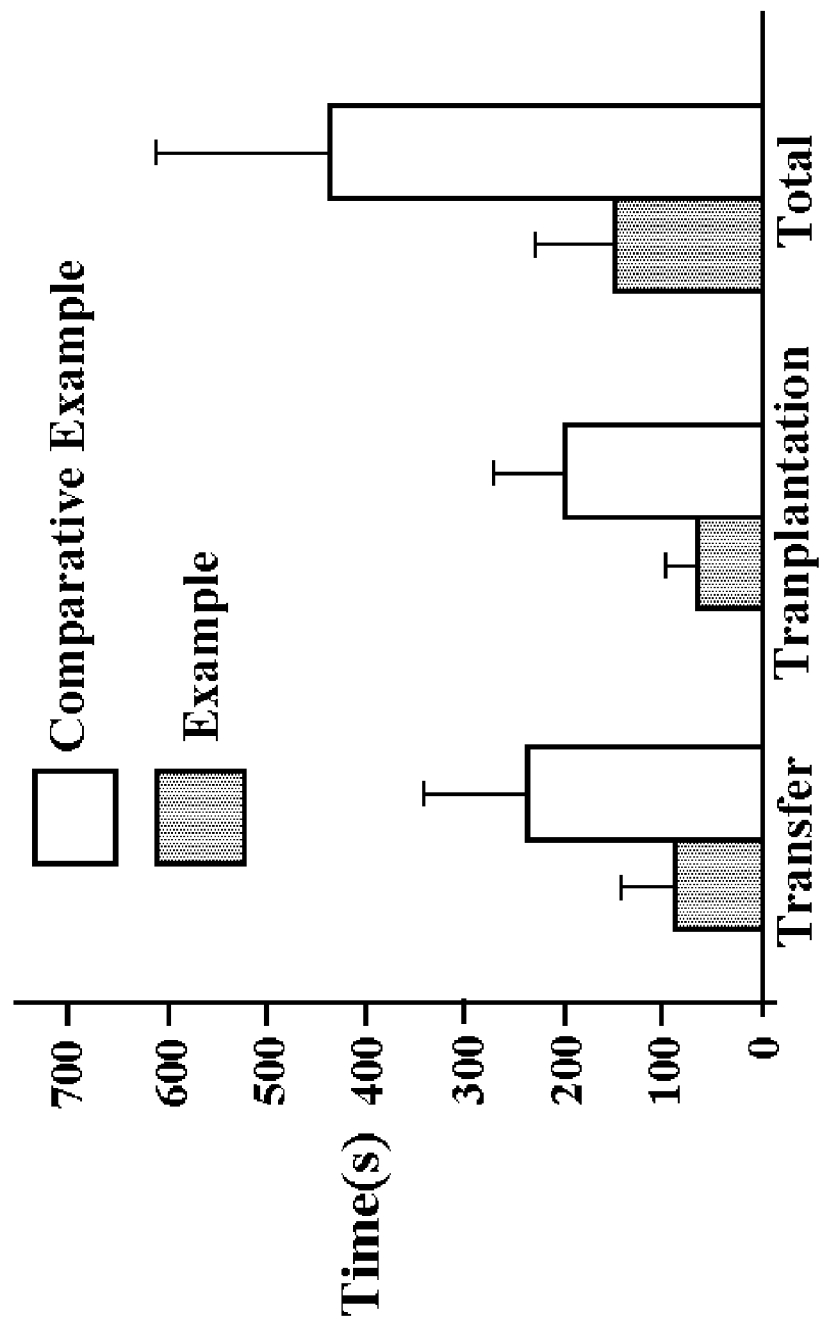
FIG. 10 represents measured results of time required for affixing a cell sheet to an esophagus wall in comparison with the embodiment of the present invention.

For Examples, works for transferring a cell sheet and applying the same onto the esophagus inner wall of the living body have been conducted to measure times required for such works (with the number of samples being 7 and shown in FIG. 10 as Examples). For Comparative Examples, times required for transfer and application upon using a method in which a cell sheet is stacked on a conventional polyvinylidene fluoride film (with the number of samples being 3 and shown in FIG. 10 as Comparative Examples). Comparison results are shown in FIG. 10. The term "Transfer" represents time required for the cell sheet to be transferred from the outside of the body to the affected area (at the inside of the esophagus) to be affixed. The term "Transplantation" represents time required only for affixing work. In the figure, ranges corresponding to variation of measured times are also indicated in error bars.

With such results, it has been confirmed that the times required for transfer and application in Examples were shortened to the extent ⅓ of the Comparative Examples in a remarkable decrease. It is apparent that even though such a therapeutic method mitigates the burden of patients as compared to that experienced in a usual surgical operation, the required times are remarkably shortened for thereby remarkably eliminating the burden of the patients.

Second Embodiment

Figure 11A:
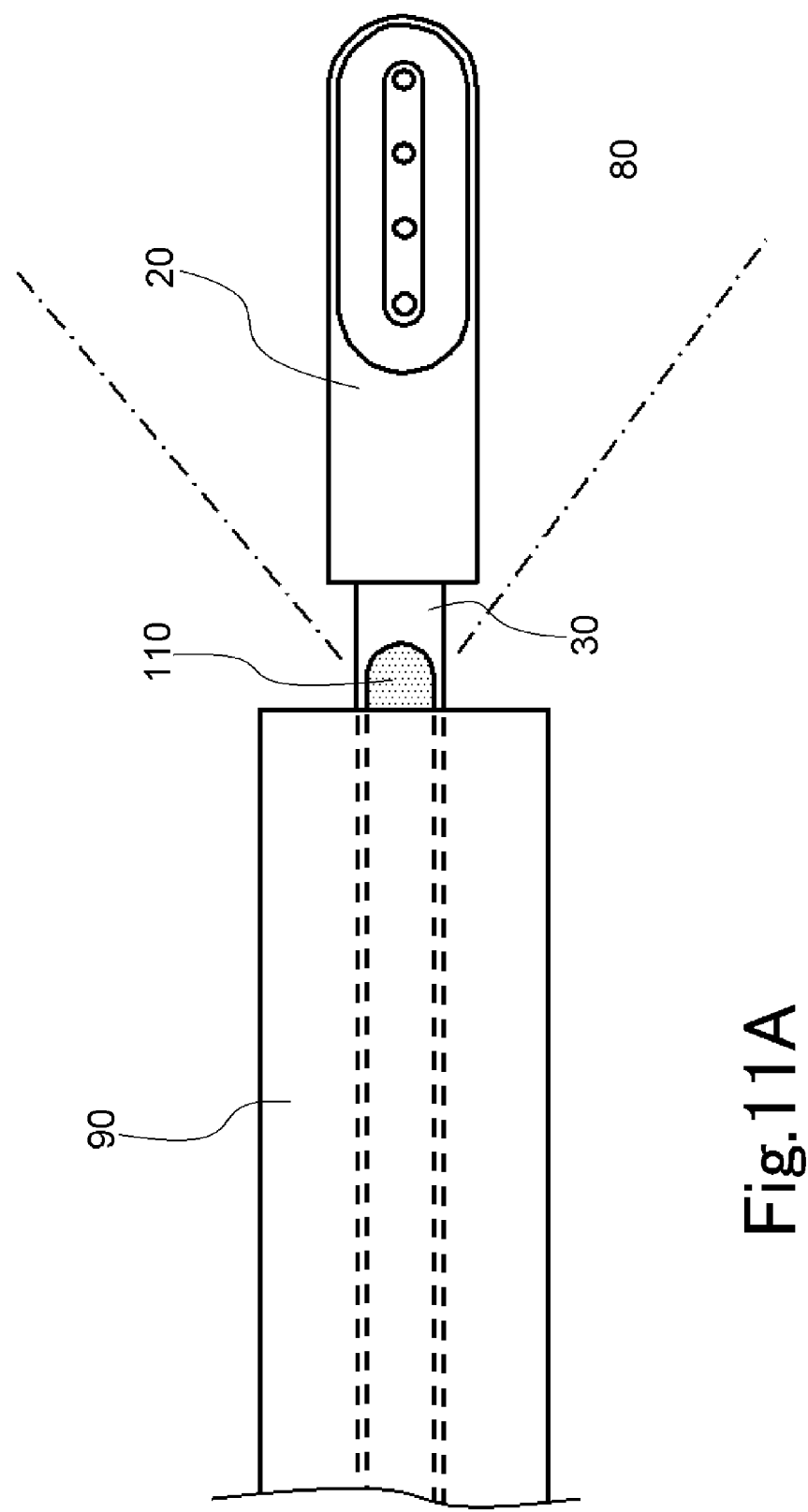
FIGS. 11A, 11B and 11C represent a top view, a side view and a cross-sectional view taken on line H-H, respectively, for showing a structure of a sheet shaped therapeutic substance transfer apparatus of a second embodiment according to the present invention.
Figure 11B:
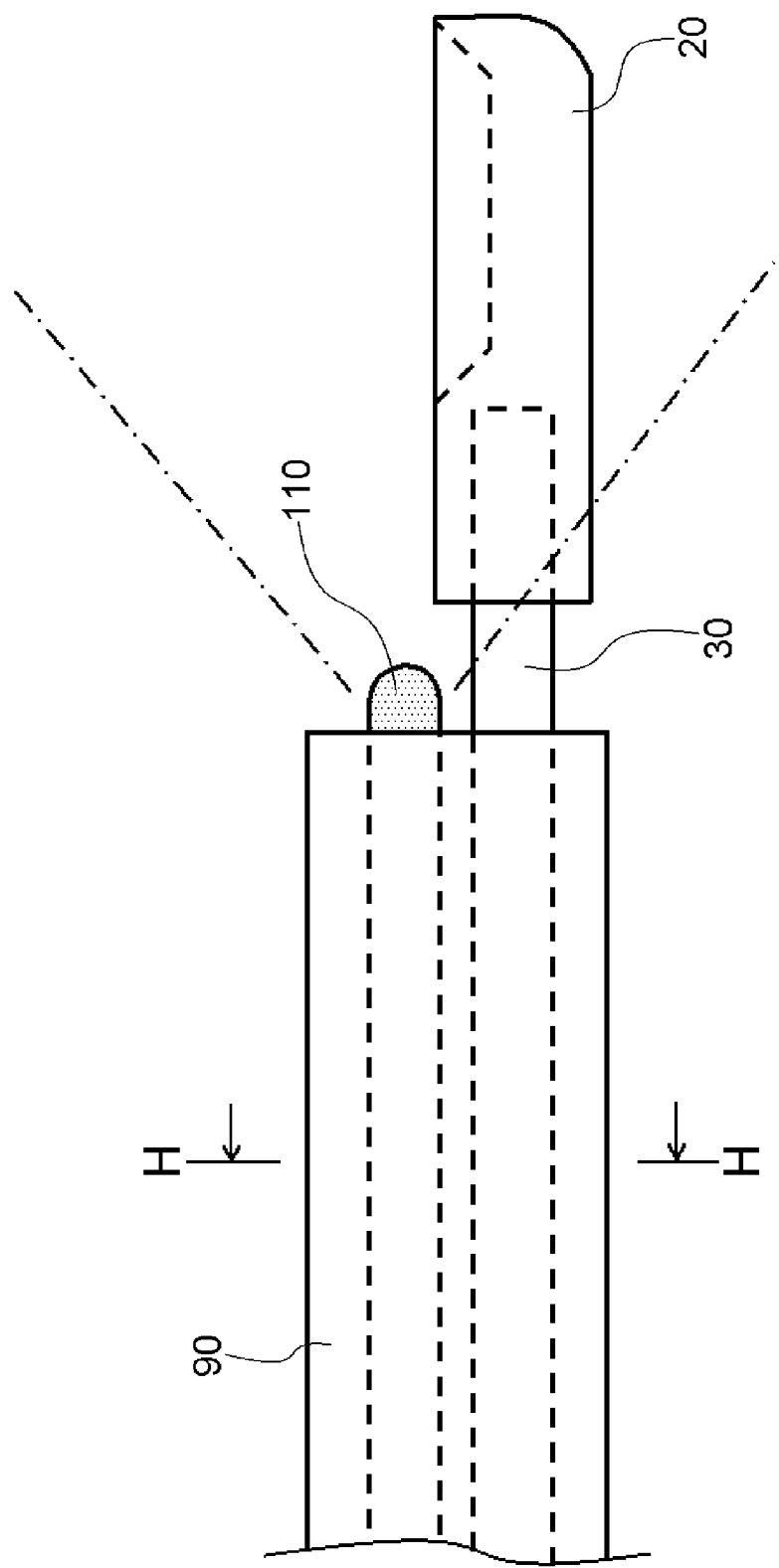
Figure 11C:
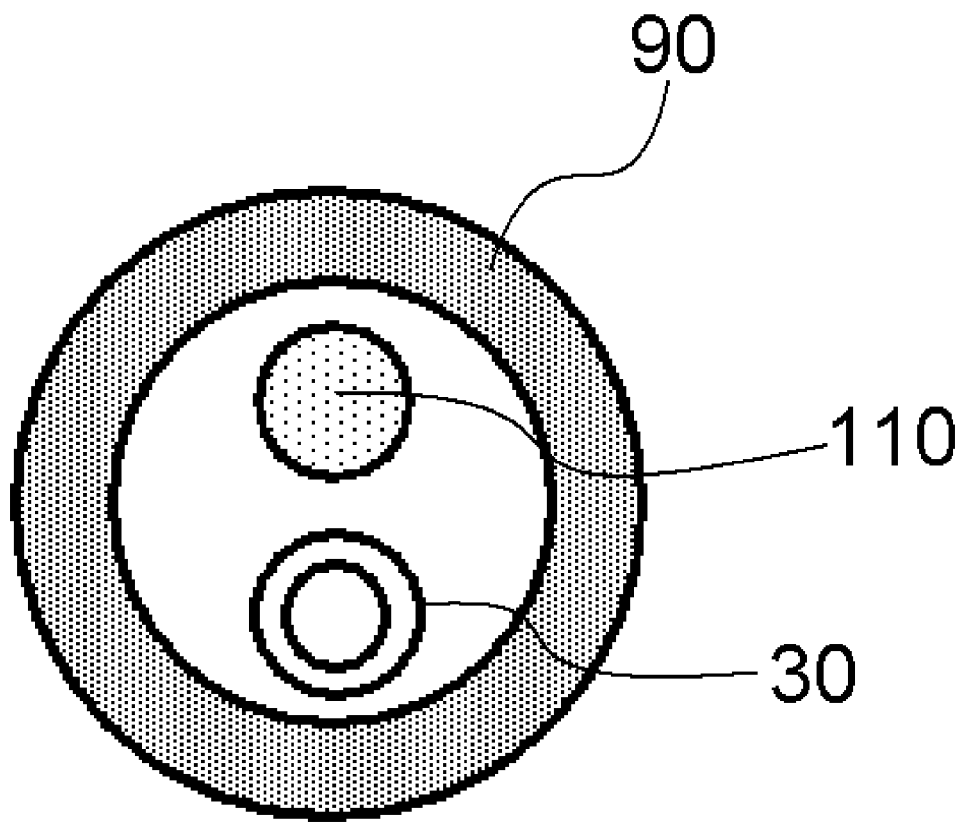

A transfer apparatus according to a second embodiment is different in structure from that of FIG. 8. An endoscope and an endoscope system, used for confirming the affected area or the like for the sheet shaped substance to be affixed and for accurately adjusting a position of ahead, are integrally formed with the transfer apparatus. FIGS. 11A, 11B and 11C represent an example of a structure that is integrally structured with the endoscope system 110, the vent pipe 30 mentioned above, the head 20 and an outer tube section 90. Here, examples of the endoscope system 10 may include various configurations involving the endoscope and, hence, the endoscope system 110 and the outer tube section 90, shown in FIGS. 11A, 11B and 11C, are integrated. This also makes it possible to provide a configuration with the vent pipe 30 and the head 20 incorporated in the endoscope system 110. In such a case, the vent pipe 30 is inserted through the endoscope system in configuration and the outer tube section 90 does not constitute an independent component part. In an example shown in FIGS. 11A, 11B and 11C, the endoscope system 110 and the outer tube section 90 are configured in independent component parts. FIG. 11A represents a top view showing the structure of the transfer apparatus 80; FIG. 11B represents a side view; and FIG. 11C represents a cross-sectional view taken on line H-H. Here, the head 20 and the vent pipe 30 are similar to those set forth above.

With such a transfer apparatus 80, the vent pipe 30 and the endoscope system 110 extend through the outer tube section (outer tube) 90. The head 2, formed at the distal end of the vent pipe 30, and a distal end of the endoscope system 110, enabling the observation of the affected area, are formed in structure to be exposed at one end of the outer tube section 90. Regions, surrounded by dot and dashed lines in FIGS. 11A and 11B, represent visual field ranges of the endoscope system 110. In addition, the endoscope system (endoscope) 110 is made available to move through the outer tube section 90 in a direction approximately parallel to the vent pipe 30. This enables a situation to be established for the endoscope system (endoscope) 110 to properly observe an area (affected area) for the sheet shaped substance to be affixed.

With the transfer apparatus 10, subsequently, the sheet shaped substance can be transferred to the living body for application with a positional relationship between the endoscope system 110 and the head 20 being fixedly secured by the outer tube section 90. When this takes place, the endoscope system 110 is located on a side at which the sheet shaped substance is blown off from the head 20. This enables the affected area and the sheet shaped substance, subsequent to blowing off step, to be observed by using the endoscope system 110. In this instance, since the head 20 is miniaturized in contrast to the apparatus described in Patent Document 3, there is nothing to obstruct a visual field even when applying the sheet shaped substance, thereby making it easy to perform such an observation.

Depending on needs, further, the outer tube section 90 may be internally provided with a tubular structure except for the vent pipe 30 and the endoscope system 110. FIG. 12 is a cross-sectional view, corresponding to FIG. 11C, which represents such a case. Here, the outer tube section 90 also internally incorporates a lighting tube 111, having a distal end for irradiating light onto the affected area, and a cleaning tube 112 having a distal end for ejecting cleaning water for cleaning a distal end of the endoscope system 110. These distal ends are configured to be exposed from one end of the outer tube section 90 in the same manner as the head 20 and the endoscope system 110. In addition, the outer tube section 90 may also be provided with other tubular structures depending on needs. The transfer apparatus 10 may be handled for each outer tube section 90. In FIG. 12, moreover, the lighting tube 111 and the cleaning tube 112 or the like may be integrally configured together with the vent pipe 30 as the endoscope system 110. On the contrary, the outer tube section 90 may be unnecessary: if a positional relationship between the endoscope system 110 and the vent pipe 30 and the head 20 can be established in the same manner as set forth above; or depending on a situation of an opening portion of the living body for the transfer apparatus to be inserted.

With such a structure set forth above, the vent pipe 30 to be used has an outer diameter that can be reduced. Even if such a tubular structure is incorporated in the outer tube section 90 at the same time, the maximum width of the whole structure can be minimized for easy insertion to the living body.

With such a structure mentioned above, furthermore, no need arises for the vent apertures, provided in plural areas, to have the same opening diameters. The opening diameters may be distributed in size such that it becomes possible to control a blowing-off direction of the sheet shaped substance with an increased accuracy of such a direction. When using a plurality of vent aperture groups, such determinations may be possibly conducted for each of the vent aperture groups.

DESCRIPTION OF REFERENCE SIGNS 10, 80 sheet shaped therapeutic substance transfer apparatus (transfer apparatus)
20, 50, 70, 75 head
21, 72 cavity portion
22, 51 concave portion
23, 52, 71 vent apertures
24 apex portion
30 vent pipe
40 sheet shaped therapeutic substance (sheet shaped substance)
90 outer tube section (outer tube)
110 endoscope (endoscope system)
111 lighting tube
112 cleaning pipe
120 forceps
200 living body
210 affected area
300 esophagus wall
521 first vent apertures
522 second vent apertures
531 first cavity portion
532 second cavity portion
541 first vent aperture portion
542 second vent aperture portion
601 first sheet shaped substance
602 second sheet shaped substance

The invention claimed is:
1. A method of affixing a sheet shaped therapeutic substance using a sheet shaped therapeutic substance transfer apparatus comprising:
 a head an inside of which is configured to be supplied with a fluid so that the sheet shaped therapeutic substance is adsorbed to the head by setting a pressure of the fluid as a negative pressure, and the adsorbed sheet shaped therapeutic substance is removed from the head by setting the pressure of the fluid as a positive pressure; and
 a vent pipe connected to the head and which is configured to supply the fluid to the head, wherein:
  a size of the vent pipe along a direction perpendicular to a longitudinal direction of the vent pipe is smaller than the size of the head along the direction perpendicular to the longitudinal direction, and
  the head has a surface formed in a convex shape, and a plurality of vent apertures to eject the fluid in a direction approximately perpendicular to a longitudinal direction of the vent pipe, is formed in the surface,
the method comprising:
 locating the head in a position in which an affected area on an inner surface of a tubular organ inside a living body and the sheet shaped therapeutic substance held by the head are in close proximity to each other with the sheet shaped therapeutic substance being held by the head, by inserting both the head and the vent pipe in the tubular organ inside the living body; and making a pressure of fluid positive for causing the sheet shaped therapeutic substance to be removed and blown off from the head for affixing the sheet shaped therapeutic substance to the affected area for the sheet shaped therapeutic substance to be affixed.

2. The method of affixing the sheet shaped therapeutic substance according to claim 1, wherein when holding the sheet shaped therapeutic substance on the head, the sheet shaped therapeutic substance is adsorbed by the vent apertures under a folded state.

3. The method of affixing the sheet shaped therapeutic substance according to claim 1, further comprising using the sheet shaped therapeutic substance transfer apparatus in combination with an endoscope, wherein during the affixing of the sheet shaped therapeutic substance, observing the affixing with the endoscope.

* * * * *